US006838489B2

(12) United States Patent
Bell et al.

(10) Patent No.: US 6,838,489 B2
(45) Date of Patent: Jan. 4, 2005

(54) HIGH ACTIVITY METAL CARBENE METATHESIS CATALYSTS GENERATED USING A THERMALLY ACTIVATED N-HETEROCYCLIC CARBENE PRECURSOR

(75) Inventors: Andrew Bell, Lakewood, OH (US); Robert H. Grubbs, South Pasadena, CA (US); John P Morgan, Pasadena, CA (US); Jason L. Moore, Huntsville, TX (US)

(73) Assignees: Cymetech, LLC, Huntsville, TX (US); California Institute of Technology, Pasadena, CA (US)

( * ) Notice: Subject to any disclaimer, the term of this patent is extended or adjusted under 35 U.S.C. 154(b) by 0 days.

(21) Appl. No.: 10/107,531

(22) Filed: Mar. 25, 2002

(65) Prior Publication Data

US 2003/0144437 A1 Jul. 31, 2003

Related U.S. Application Data

(60) Provisional application No. 60/288,680, filed on May 3, 2001, provisional application No. 60/278,311, filed on Mar. 23, 2001, and provisional application No. 60/360,775, filed on Mar. 1, 2002.

(51) Int. Cl.[7] ............................... C08F 2/46; C08F 2/48; C08F 4/44
(52) U.S. Cl. .............................. 522/63; 522/64; 522/65; 526/171; 526/172; 526/280; 526/281; 526/335
(58) Field of Search .............................. 522/63, 64, 65; 526/171, 172, 280, 281, 335; 548/101, 262.2; 556/136, 22; 502/155

(56) References Cited

U.S. PATENT DOCUMENTS

| 4,161,528 A | 7/1979 | Thomas et al. ............. 424/273 |
| 4,301,306 A | 11/1981 | Layer ......................... 568/734 |
| 4,324,717 A | 4/1982 | Layer ......................... 524/244 |
| 5,312,940 A | 5/1994 | Grubbs et al. ............... 556/136 |
| 5,342,909 A | 8/1994 | Grubbs et al. ............... 526/171 |
| 5,468,819 A | 11/1995 | Goodall et al. ............. 526/171 |
| 5,545,790 A | 8/1996 | Wu et al. .................... 585/510 |
| 5,569,730 A | 10/1996 | Goodall et al. ............. 526/282 |

(List continued on next page.)

FOREIGN PATENT DOCUMENTS

| EP | 0 798 041 | 10/1997 | |
| WO | WO 95/14048 | 5/1995 | ........... C08F/32/08 |
| WO | WO 96/37526 | 11/1996 | ........... C08F/32/00 |
| WO | WO 97/20865 | 6/1997 | ............. C08F/4/80 |
| WO | WO 97/20871 | 6/1997 | ......... C08F/232/08 |
| WO | WO 97/29135 | 8/1997 | ............. C08F/4/80 |
| WO | WO 97/33198 | 9/1997 | ........... G03F/7/039 |
| WO | WO 99/14256 | 3/1999 | ........... C08G/61/08 |
| WO | WO 99/51344 | 10/1999 | ........... B01J/31/22 |
| WO | WO 00/15339 | 3/2000 | ........... B01J/31/00 |
| WO | WO 00/20472 | 4/2000 | ........... C08F/32/08 |
| WO | WO 00/58322 | 10/2000 | ........... C07F/15/00 |

OTHER PUBLICATIONS

Sanford, et al. "New Insights into the Mechanism of Ruthenism–Catalyzed Olefin Metathesis Reactions" J. Am. Chem Soc. 2001, 123, ppg. 749–750.
Scholl, et al. "Synthesis and Activity of a New Generation of Ruthenium–Based Olefin Metathesis Catalysts Coordinated with 1,3–Dimesityl–4,5–dihydroimidazol–2ylidene Ligands" Organic Letters (1999), 1(16), pp 953–956.
Morgan et al. "In Situ Preparation of a Highly Active N–Heterocyclic Carbene–Coordinated Olefin Metathesis Catalyst" Organic Letters (2000), 2(20), pp. 3153.
Louie, et al., "Highly Active Metathesis Catalysts Generated In Situ from Inexpensive and Air–Stable Precursors" Chem. Int. Ed., 2001, 40, pp. 247.
Scholl et al., "Increased Ring Closing Metathesis Activity of Ruthenium–Based Olefin Metathesis Catalysts Coordinated with Imidazolin–2–ylidene Ligands," *Tetrahedron Letters* (1999) 40:2247–2250.
Jafarpour et al., "Simple and Convenient Synthetic Procedure Leading to Ruthenium Olefin Metathesis Catalysts Bearing the N,N–Bis(mesityl)imidazol–2–ylidene (IMes) Ligand," *Organometallics* (2000) 19:2055–2057.
Ulman et al., "Ruthenium Carbene–Based Olefin Metathesis Initiators: Catalysts Decomposition and Longevity," *J. Org. Chem.* (1999) 64:7202–7207.
Huang et al., "Olefin Metathesis–Active Ruthenium Complexes Bearing a Nucleophilic Carbene Ligand," *J. Am. Chem. Soc.* (1999) 121:2674–2678.
Buchmeiser, "Homogeneous Metathesis Polymerization by Well–Defined Group VI and Group VIII Transition–Metal Alkylidenes: Fundamentals and Applications in the Preparation of Advanced Materials," *Chem. Rev.* (2000) 100:1565–1604.
Bourissou et al., "Stable Carbenes," *Chem. Rev.* (2000) 100:39–91.
Arduengo, III, "Looking for Stable Carbenes: The Difficulty in Starting Anew," *Accounts of Chemical Research* (1999) 32:913–921.

*Primary Examiner*—Robert D. Harlan
(74) *Attorney, Agent, or Firm*—David Jaffer; Pillsbury Winthrop LLP

(57) ABSTRACT

The invention provides a method for converting a less active or slower to initiate system to a higher activity system so that at the end of a polymerization the most active species is present in the system. The invention generally relates to a process for converting a less active or slower to initiate catalyst system to a higher activity catalyst system wherein the process comprises contacting a protected N-heterocyclic carbene with a metathesis catalyst and an olefin in the presence of energy. One of the benefits of the invention is that the amount of catalyst required is less than or lowered in the presence of the protected N-heterocyclic carbene as compared to the amount of catalyst required in the absence of the protected N-heterocyclic carbene. The protected N-heterocyclic carbene can be unsaturated or saturated. In addition, the invention describes novel ruthenium initiators and methods of making the same.

28 Claims, No Drawings

U.S. PATENT DOCUMENTS

| | | | |
|---|---|---|---|
| 5,571,881 A | 11/1996 | Goodall et al. | 526/171 |
| 5,705,503 A | 1/1998 | Goodall et al. | 526/281 |
| 5,710,298 A | 1/1998 | Grubbs et al. | 556/22 |
| 5,728,917 A | 3/1998 | Grubbs et al. | 585/653 |
| 5,750,815 A | 5/1998 | Grubbs et al. | 585/511 |
| 5,831,108 A | 11/1998 | Grubbs et al. | 556/21 |
| 5,922,863 A | 7/1999 | Grubbs et al. | 540/538 |
| 6,107,420 A | 8/2000 | Grubbs et al. | 526/73 |
| 6,426,419 B1 * | 7/2002 | Grubbs et al. | 548/101 |

* cited by examiner

HIGH ACTIVITY METAL CARBENE METATHESIS CATALYSTS GENERATED USING A THERMALLY ACTIVATED N-HETEROCYCLIC CARBENE PRECURSOR

This application claims the benefit of U.S. Provisional Patent Application No. 60/278,311, filed Mar. 23, 2001 and entitled High Activity Ru Alkylidene & Vinylidene Derivatives Suitable for Olefin Metathesis Generated using a Thermally Deprotectable N-Heterocyclic Carbene; U.S. Provisional Patent Application No. 60/288,680, filed May 3, 2001 and entitled High Activity Group 8 Alkylidene and Vinylidene Derivatives Suitable for Olefin Metathesis Generated Using a Thermally Activated N-Heterocyclic Carbene (NHC) Precursor"; and U.S. Provisional Patent Application No. 60/360,775, filed Mar. 1, 2002 and entitled "Polymer Processing Methods and Techniques Using Pentacoordinated or Hexacoordinated Ruthenium or Osmium Metathesis Catalysts", the contents of each of which are incorporated herein by reference.

BACKGROUND

Metathesis catalysts have been previously described by for example, U.S. Pat. Nos. 5,312,940, 5,342,909, 5,728,917, 5,750,815, 5,710,298, and 5,831,108 and PCT Publications WO 97/20865 and WO 97/29135 the contents of each of which are incorporated herein by reference. These publications describe well-defined single component ruthenium or osmium catalysts that possess several advantageous properties. For example, these catalysts are tolerant to a variety of functional groups and generally are more active than previously known metathesis catalysts. The ruthenium and osmium complexes disclosed in these patents all possess metal centers that are formally in the +2 oxidation state, have an electron count of 16, and are pentacoordinated. These complexes possess the following general structure,

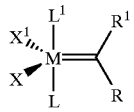

and are useful as initiators in the ring-opening metathesis polymerization (ROMP) of strained cycloolefins, such as norbornene, dicyclopentadiene, tricyclopentadiene, and functionalized norbornenes. The ring-opening metathesis polymerization (ROMP) of and addition polymerization of polycyclic olefins is depicted generally in the following reaction schemes:

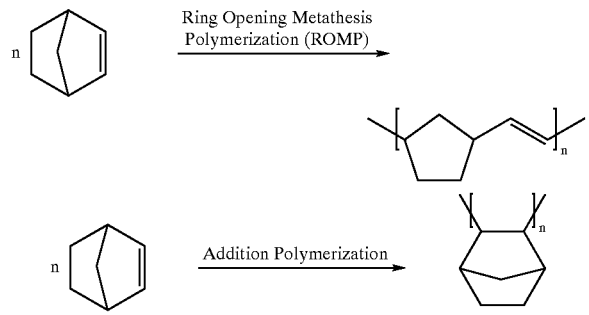

These compounds are also useful entry complexes for other metathesis reactions, including, for example, addition polymerization metathesis, ring-closing metathesis (RCM), acyclic diene metathesis (ADMET), cross-metathesis (CM) and degenerative olefin metathesis (OM).

In particular, U.S. Pat. Nos. 5,312,940 and 5,342,909 describe the synthesis of $Ru(X)(X^1)(L)(L^1)(=C((R)(R^1))$ and their related ring-opening metathesis polymerization (ROMP) activity. In these patents, L and $L^1$ are both Lewis base ligands. Further, in each of these patents the preferred Lewis base is triphenylphosphine. Subsequently, U.S. Pat. No. 5,922,863, the contents of which are incorporated herein by reference, discloses that the substitution of triarylphosphine by the more basic secondary alkyl or cycloalkylphosphines results in improved olefin metathesis activity.

It is now well recognized that one of the more active ruthenium initiator species for olefin metathesis contains a saturated or an unsaturated N- heterocyclic carbene (NHC) moiety. The increased activity of this moiety is reported in, for example, PCT Publications WO 99/51344, WO 00/15339, WO 00/15339, and WO 00/58322, the contents of each of which are incorporated herein by reference.

To date, the preferred initiators for the ROMP of dicyclopentadiene are those possessing two tertiary phosphine ligands ($PR_3$) and those possessing one NHC and one tertiary phosphine ($PR_3$), i.e.,

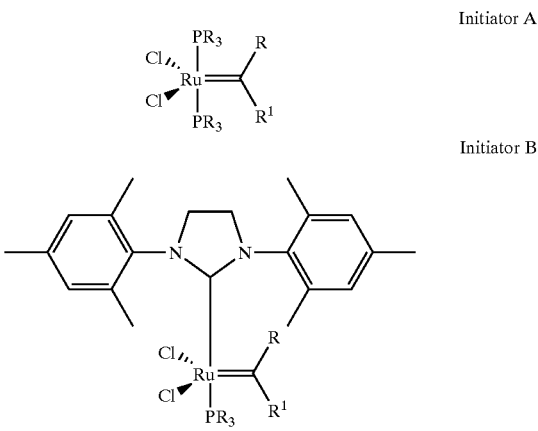

A representative Initiator A can be prepared using a "one-pot method" in almost quantitative yield from [Ru (COD)Cl$_2$]$_n$ and tricyclopentylphosphine in the presence of hydrogen and 3-chloro-3-methyl-1-butyne. A representative Initiator B is prepared from $RuCl_2(PCy_3)_2(=CHPh)$ (prepared from $RuCl_2(PPh_3)_3$ and phenyldiazomethane and the subsequent addition of tricyclohexylphosphine) via a 1,3-bis(2,4,6-trimethylphenyl)-4,5-dihydroimidazol-2-ylidene for tricyclohexylphosphine ligand exchange in toluene at about 80° C. Under typical ROMP conditions, Initiator A is capable of polymerizing DCPD effectively at generally about 7500:1 (DCPD:Ru (mole ratio)) and further conversion may be accomplished through additional post curing of the object. Alternatively, Initiator B can be employed at levels up to about 100,000:1 (DCPD:Ru (mole ratio)) and does not require a post cure step. Currently, it is more cost effective to manufacture Initiator A in place of Initiator B, but the high catalyst efficiency is not reached, i.e., conversion of monomer to polymer, and posturing of polyDCPD parts is commonplace. One disadvantage to the use of well-defined alkylidene catalysts such as Initiator A and B is that they initiate polymerization (or olefin metathesis) immediately upon contact with a metathesizable monomer. Another drawback of the Initiator B type species is that such species are sensitive to the reaction temperature in comparison to the Initiator A type, so that a reaction medium of polycyclic olefin gels or "sets up" more rapidly. The high activity of Initiator B is preferred over Initiator A, but the processability of Initiator A is preferred over Initiator B. Initiator B is also more resistant to atmospheric (oxygen and water), temperature, and monomer impurities than Initiator A.

It has been reported in the literature, in for example, M. A. Sanford, M. Ulman, and R. H. Grubbs, J. Am. Chem. Soc, 2001, 123, 749–750, the contents of which are herein incorporated by reference, that the high activity for the NHC carbene coordinated initiator (Initiator B), which had been attributed to its ability to promote phosphine dissociation, instead appears to be due to the improved selectivity for binding π-acidic olefinic substrates in the presence of a σ-donating free phosphine. Also, the addition of Lewis bases to Initiator A can further slow the initiation process of the polymerization because of the competition between the olefin and the Lewis base.

Transition metal derivatives and initiator precursors useful in the addition polymerization of norbornene and substituted norbornenes ("polycyclic olefins") are described in U.S. Pat. Nos. 5,705,503; 5,571,881; 5,569,730; and 5,468,819 and in PCT Publications WO 97/20871; WO 00/34344; WO 00/20472; WO 99/14256; WO 96/37526; WO 97/20871; WO 97/33198; WO 95/14048; and WO 97/33198, the contents of each of which are herein incorporated by reference.

The thermal conversion of 1,3-diphenyltrichloromethylimidazoline is shown in Scheme 2:

SCHEME 2

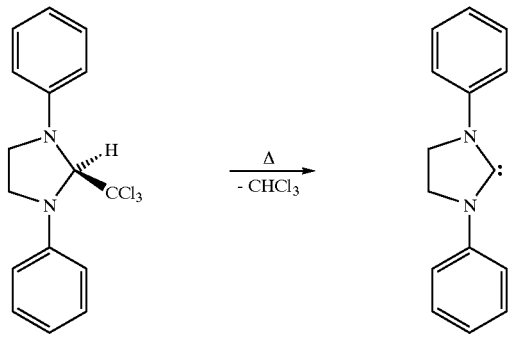

Similarly, 1,3-diphenyl-2-alkoxyimidazolidine, i.e., 2-methoxy-1,3-diphenylimidazolidine and 2-(benzyloxy)-1,3-diphenyl-imidazolidine, can lose alcohols (anomalous α-elimination) upon heating to give 1,3-diphenylimidazolidin-2-ylidene.

In addition, in-situ deprotection to perform a ligand switch at a metal occurs during the thermal deprotection of 1,3-diphenyl-2-trichloromethylimidazolidine in refluxing xylene in combination with di-μ-chlorobis(triethylphosphine)diplatinum to generate trans-dichloro(1,3-diphenylimidazolidin-2-ylidene)(triethylphosphine)platinum(II). Similarly, bis(1,3-diaryl) and bis(1,3-diaralkyl)-imidazolidinylidene compounds (bis-NHC carbene precursors) may be employed in the generation of ruthenium, platinum, and palladium compounds containing an imidazolidin-2-ylidene moiety.

In addition, there have been some ligand exchange reactions based, e.g., triarylphosphine substitution by imidazolidine, at a metal center employing "transient" or "in-situ"-generated, ether protected, substituted and unsubstituted imidazolidines, i.e.,

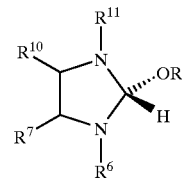

Further, Grubbs described in Organic Letters (1999), 1(16), 953–956, that the alkoxy-protected NHC species did not react with benzylidene ruthenium complexes in solvent at ambient temperature; however, they readily reacted with $RuCl_2(PR_3)_2(=CHR)$ when deprotected in situ by heating to 60–80° C. However, the isolation of these alkylidenes generally requires air-free, anhydrous conditions, and multiple purifications to remove the displaced trialkylphosphine.

R. H. Grubbs and M. Scholl describe the method of making compounds of the following formula in PCT publication WO 00/71554, the contents of which are herein incorporated by reference:

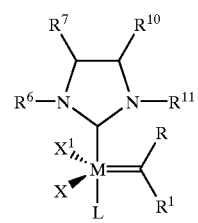

The ruthenium or osmium complexes employed were of the identity $MCl_2L_2(=C(R)(R^1))$, where L is a Lewis base. The ether-based imidazolidine is prepared as shown in the following scheme:

SCHEME 3

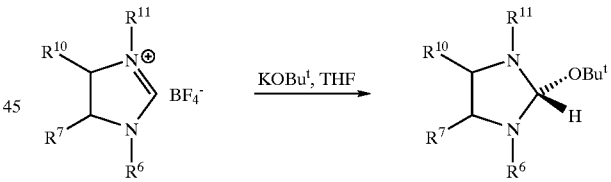

However, in these systems, the ether is not isolated, but used in-situ. The deprotection step occurs most efficiently when heating the ether derivative and the free imidazolidine NHC is generated and replaces the ligand at the metal complexes within about ten minutes. Representative examples of suitable bases include t-BuOK/THF, t-BuONa/THF, and $NaOCH_3/CH_3OH$.

The in situ preparation of a highly active N-heterocyclic carbene-coordinated olefin metathesis catalyst has been described by Morgan and Grubbs, Org. Letters. (2000), 2(20), 3153, the contents of which are incorporated herein by reference, for cross and ring-closing metathesis reactions. The paper disclosed that the high activity ruthenium alkylidene initiators could be generated without requiring prior isolation of the catalyst. However, the activation of this in situ catalyst with HCl or other phosphine scavengers was useful to improve the reaction times required for high conversions and to overcome the phosphine inhibition.

Furthermore, the NHC precursor in this system was not isolated, but generated in solvent, e.g.,

SCHEME 4

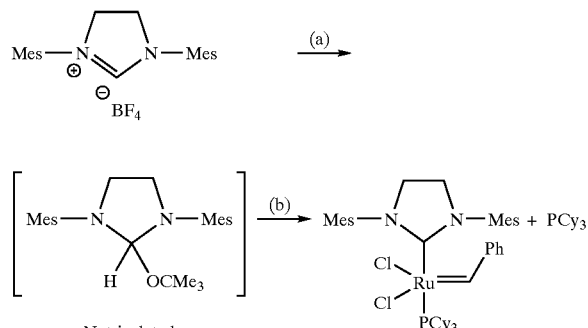

Not isolated
(a) KOBu$^t$, THF, less than 1 min at 25° C.;
(b) RuCl$_2$(PCy$_3$)$_x$(═CHPh), 80° C., 30 min. to generate a mixture of RuCl$_2$(s-Imes)(PCy$_3$)(═CHPh and 1 equiv of PCy$_3$.

It would therefore be desirous to be able to convert a less active (i.e., slower to initiate) system, such as Initiator A, to a higher activity system, i.e., Initiator B, so that at the end of a polymerization the most active species is present in the system. Such reactions would be expected to be slow at their start allowing improved pot life, and, yet, at the end of the reaction, allow for excellent monomer to polymer conversion. Further, the more thermally stable Initiator B species would be longer lived at the high temperatures associated with the ROMP of polycyclic olefins. Additionally, it is of benefit to have a synthetic method to generate species such as Initiator B which (i) uses readily available ingredients, (ii) reduces the number of synthetic steps, (iii) eliminates the need for a phosphine exchange, (iv) eliminates the separation of by-products, and (v) yields an initiator with the appropriate ligand set in high yield.

The invention overcomes the shortcomings of the prior art by providing a method which moderates a cyclic olefin polymerization reaction (ROMP or Addition, for example) through the use of a protected NHC, while obtaining excellent monomer to polymer conversion. The invention accomplishes this by using the polymerization exotherm generated by a ROMP initiator or addition initiator to be the source of energy for deprotecting a NHC—X$^2$—Y reagent which, in turn, enhances the activity of the initial polymerization (ROMP or Addition Polymerization, for example) initiator. The reagent described herein is an air-stable, isolable, and deprotectable NHC reagent, i.e., NHC—X$^2$—Y. In addition, the invention provides new NHC ruthenium alkylidene initiator identities, and new synthetic routes to ruthenium initiators.

In particular, the invention is related to the in-situ preparation of NHC metal carbene metathesis catalyst species in polycyclic olefin formulations, which exhibit comparable activity to those previously described. Yet the inventive methods do not require extensive purification under rigorously air- and moisture-free conditions nor the removal of free phosphine ligand and are prepared from stable and isolable starting complexes.

SUMMARY

The invention provides a method for converting a less active or slower to initiate system to a higher activity system so that at the end of a polymerization the most active species is present in the system. The invention generally relates to a process for converting a less active or slower to initiate catalyst system to a higher activity catalyst system wherein the process comprises contacting a protected N-heterocyclic carbene with a metathesis catalyst and an olefin in the presence of energy. One of the benefits of the invention is that the amount of catalyst required is less than or lowered in the presence of the protected N-heterocyclic carbene as compared to the amount of catalyst required in the absence of the protected N-heterocyclic carbene. The protected N-heterocyclic carbene can be unsaturated or saturated. In addition, the invention describes novel ruthenium initiators and methods of making the same.

DETAILED DESCRIPTION OF THE PREFERRED EMBODIMENTS

The invention provides a method for converting a less active or slower to initiate system to a higher activity system so that at the end of a polymerization the most active species is present in the system. The invention generally relates to a process for converting a less active or slower to initiate catalyst system to a higher activity catalyst system wherein the process comprises contacting a protected N-heterocyclic carbene with a metathesis catalyst and an olefin in the presence of energy. One of the benefits of the invention is that the amount of catalyst required is less than or lowered in the presence of the protected N-heterocyclic carbene as compared to the amount of catalyst required in the absence of the protected N-heterocyclic carbene. The terms "catalyst," "initiator" and "complex" herein are used interchangeably.

Unmodified ruthenium and osmium carbene complexes have been described in U.S. Pat. Nos. 5,312,940, 5,342,909, 5,728,917, 5,750,815, and 5,710,298, all of which are incorporated herein by reference. The ruthenium and osmium carbene complexes disclosed in these patents all possess metal centers that are formally in the +2 oxidation state, have an electron count of 16, and are penta-coordinated. These catalysts are of the general formula

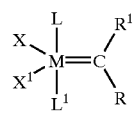

wherein:
M is ruthenium or osmium;
X and X$^1$ are the same or different and are each independently any anionic ligand;
L and L$^1$ are the same or different and are each independently any neutral electron donor ligand;
R and R$^1$ are the same or different and are each independently hydrogen or a substituent selected from the group consisting of C$_1$–C$_{20}$ alkyl, C$_2$–C$_{20}$ alkenyl, C$_2$–C$_{20}$ alkynyl, aryl, C$_1$–C$_{20}$ carboxylate, C$_1$–C$_{20}$ alkoxy, C$_2$–C$_{20}$ alkenyloxy, C$_2$–C$_{20}$ alkynyloxy, aryloxy, C$_2$–C$_{20}$ alkoxycarbonyl, C$_1$–C$_{20}$ alkylthio, C$_1$–C$_{20}$ alkylsulfonyl, C$_1$–C$_{20}$ alkylsulfinyl, and silyl. Optionally, each of the R or R$^1$ substituent group may be substituted with one or more moieties selected from the group consisting of C$_1$–C$_{10}$ alkyl, C$_1$–C$_{10}$ alkoxy, and aryl which in turn may each be further substituted with one or more groups selected from a halogen, a C$_1$–C$_5$ alkyl, C$_1$–C$_5$ alkoxy, and phenyl. Moreover, any of the catalyst ligands may further include one or more functional groups. Examples of suitable functional groups include but are not limited to: hydroxyl, thiol, alcohol, sulfonic acid, phosphine, thioether, ketone, aldehyde, ester, ether, amine, imine, amide, imido, nitro, carboxylic acid, disulfide, carbonate, isocyanate, carbodiimide, carboalkoxy, carbamate, acetal, ketal, boronate, cyano, cyanohydrin, hydrazine, oxime, hydrazide, enamine, sulfone, sulfide, sulfenyl, and halogen.

The catalysts having a higher activity system are as described above except that $L^1$ may be an unsubstituted or substituted imidazolidine,

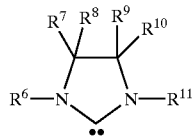

resulting in a complex of the general formula

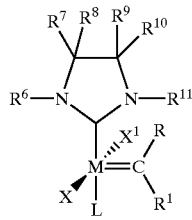

wherein:

$R^6$, $R^7$, $R^8$, $R^9$, $R^{10}$ and $R^{11}$ are each independently hydrogen or a substituted or unsubstituted substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_1$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl, $C_1$–$C_{20}$ alkylsulfinyl, and silyl. Optionally, each of the $R^6$, $R^7$, $R^8$, $R^9$, $R^{10}$ and $R^{11}$ substituent groups may be substituted with one or more moieties selected from the group consisting of $C_1$–$C_{10}$ alkyl, $C_1$–$C_{10}$ alkoxy, and aryl which in turn may each be further substituted with one or more groups selected from a halogen, a $C_1$–$C_5$ alkyl, $C_1$–$C_5$ alkoxy, and phenyl. Moreover, any of the $R^6$, $R^7$, $R^8$, $R^9$, $R^{10}$ and $R^{11}$ substituent groups may further include one or more functional groups. Examples of suitable functional groups include but are not limited to: hydroxyl, thiol, alcohol, sulfonic acid, phosphine, thioether, ketone, aldehyde, ester, ether, amine, imine, amide, imide, imido, nitro, carboxylic acid, disulfide, carbonate, isocyanate, carbodiimide, carboalkoxy, carbamate, acetal, ketal, boronate, cyano, cyanohydrin, hydrazine, oxime, hydrazide, enamine, sulfone, sulfide, sulfenyl, and halogen.

Alternatively, the unsubstituted or substituted imidazolidine may be unsaturated resulting in a complex of the general formula:

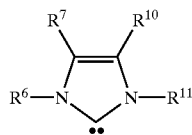

wherein $R^6$, $R^7$, $R^{10}$ and $R^{11}$ are as defined above.

In certain preferred embodiments of these catalysts, the R substituent is hydrogen and the $R^1$ substituent is selected from the group consisting of $C_1$–$C_{20}$ alkyl, $C_2$–$C_{20}$ alkenyl, and aryl. In even more preferred embodiments, the $R^1$ substituent is phenyl or vinyl, optionally substituted with one or more moieties selected from the group consisting of $C_1$–$C_5$ alkyl, $C_1$–$C_5$ alkoxy, phenyl, and a functional group. In especially preferred embodiments, $R^1$ is phenyl or vinyl substituted with one or more moieties selected from the group consisting of chloride, bromide, iodide, fluoride, —$NO_2$, —$NMe_2$, methyl, methoxy and phenyl. In the most preferred embodiments, the $R^1$ substituent is phenyl or —C=C(CH$_3$)$_2$.

In preferred embodiments of these catalysts, L is selected from the group consisting of phosphine, sulfonated phosphine, phosphite, phosphinite, phosphonite, arsine, stibine, ether, amine, amide, imine, sulfoxide, carboxyl, nitrosyl, pyridine, and thioether. In more preferred embodiments, L is a phosphine of the formula $PR^3R^4R^5$, where $R^3$, $R^4$, and $R^5$ are each independently aryl or $C_1$–$C_{10}$ alkyl, particularly primary alkyl, secondary alkyl or cycloalkyl. In the most preferred embodiments, L is each selected from the group consisting of —P(cyclohexyl)$_3$, —P(cyclopentyl)$_3$, —P(isopropyl)$_3$, and —P(phenyl)$_3$.

In preferred embodiments of these catalysts, X and $X^1$ are each independently hydrogen, halide, or one of the following groups: $C_1$–$C_{20}$ alkyl, aryl, $C_1$–$C_{20}$ alkoxide, aryloxide, $C_3$–$C_{20}$ alkyldiketonate, aryldiketonate, $C_1$–$C_{20}$ carboxylate, arylsulfonate, $C_1$–$C_{20}$ alkylsulfonate, $C_1$–$C_{20}$ alkylthio, $C_1$–$C_{20}$ alkylsulfonyl, or $C_1$–$C_{20}$ alkylsulfinyl. Optionally, X and $X^1$ may be substituted with one or more moieties selected from the group consisting of $C_1$–$C_{10}$ alkyl, $C_1$–$C_{10}$ alkoxy, and aryl which in turn may each independently be further substituted with one or more groups selected from halogen, $C_1$–$C_5$ alkyl, $C_1$–$C_5$ alkoxy, and phenyl. In more preferred embodiments, X and $X^1$ are halide, benzoate, $C_1$–$C_5$ carboxylate, $C_1$–$C_5$ alkyl, phenoxy, $C_1$–$C_5$ alkoxy, $C_1$–$C_5$ alkylthio, aryl, and $C_1$–$C_5$ alkyl sulfonate. In even more preferred embodiments, X and $X^1$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethanesulfonate. In the most preferred embodiments, X and $X^1$ are each chloride.

In preferred embodiments of the catalysts, $R^7$ and $R^{10}$ are each independently hydrogen, phenyl, or together form a cycloalkyl or an aryl optionally substituted with one or more moieties selected from the group consisting of $C_1$–$C_{10}$ alkyl, $C_1$–$C_{10}$ alkoxy, aryl, and a functional group selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen; and $R^6$ and $R^{11}$ are each is independently $C_1$–$C_{10}$ alkyl or aryl optionally substituted with $C_1$–$C_5$ alkyl, $C_1$–$C_5$ alkoxy, aryl, and a functional group selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

In more preferred embodiments, $R^7$ and $R^{10}$ are both hydrogen or phenyl, or $R^7$ and $R^{10}$ together form a cycloalkyl group; if present, $R^8$ and $R^9$ are each hydrogen; and $R^6$ and $R^{11}$ are each either substituted or unsubstituted aryl. Without being bound by theory, it is believed that bulkier $R^1$ and $R^{11}$ groups result in catalysts with improved characteristics such as thermal stability. In especially preferred embodiments, $R^6$ and $R^{11}$ are the same and each is independently of the formula

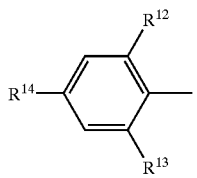

wherein:

$R^{12}$, $R^{13}$, and $R^{14}$ are each independently hydrogen, $C_1$–$C_{10}$ alkyl, $C_1$–$C_{10}$ alkoxy, aryl, or a functional group selected from hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen. In especially preferred embodiments, $R^{12}$, $R^{13}$, and $R^{14}$ are each independently selected from the group consisting of hydrogen, methyl, ethyl, propyl, isopropyl, hydroxyl, and halogen. In the most preferred embodiments, $R^{12}$, $R^{13}$, and $R^{14}$ are the same and are each methyl.

Examples of the preferred embodiments of these catalysts include:

1

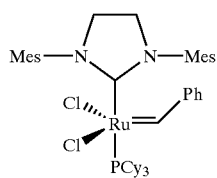

2

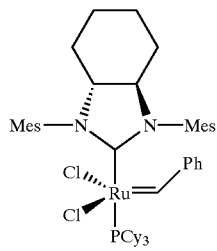

3

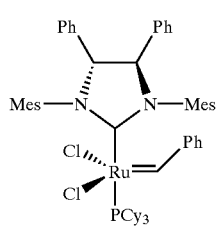

4

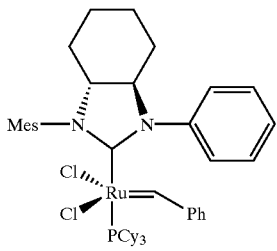

5

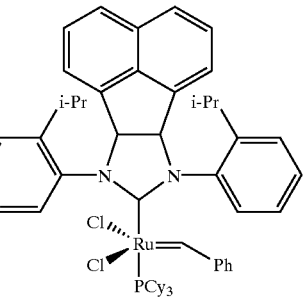

6

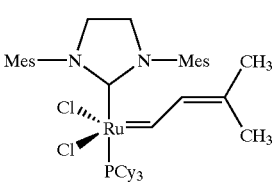

7

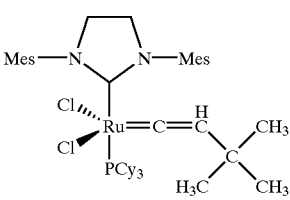

wherein Mes is

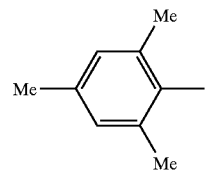

(also known as "mesityl"); i-Pr is isopropyl; and $PCy_3$ is —P(cyclohexyl)$_3$.

The inclusion of an imidazolidine ligand to the previously described ruthenium or osmium catalysts has been found to dramatically improve the properties of these complexes. The catalyst maintains the functional group tolerance of previously described ruthenium complexes while having enhanced metathesis activity that compares favorably to prior art tungsten and molybdenum systems.

Additionally, Grubbs and Tmka in PCT Publication WO 00/58322 entitled, "Novel Ruthenium Metal Alkylidene Complexes Coordinated With Triazolylidene Ligands That Exhibit High Olefin Metathesis Activity," the contents of which are incorporated herein by reference, discloses ruthenium alkylidene of the type $(PCy_3)(L)Cl_2Ru(=CHPh)$ (L=triazolylidene ligand). As shown in Scheme 5, the triazolylidene ligand is generated in-situ by the elimination of alcohol from the corresponding 5-methoxytriazole:

SCHEME 5

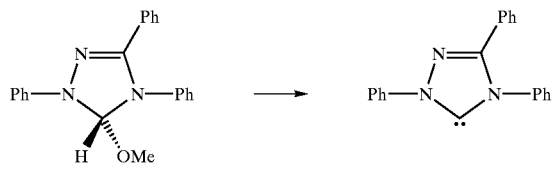

These catalysts have been considerably more active for olefin metathesis at elevated temperatures than the parent catalyst Ru(PCy$_3$)$_2$Cl$_2$(=CHPh) (2) or type A initiator. For example, 1 (L=1,4,4-triphenyl-4,5-dihydro-1H-triazol-5-ylidene) is able to catalyze the ring-closing metathesis of substituted dienes to give tetra-substituted cyclic olefins in good yield. In addition, this complex demonstrates the analogous stability towards oxygen and moisture exhibited by catalysts of the general formula:

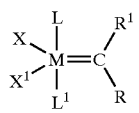

J. Louie and R. H. Grubbs have reported the in situ synthesis of a highly active metathesis catalyst prepared from inexpensive and air-stable precursors in Angew. Chem. Int. Ed., 2001, 40, 247, the contents of which are incorporated herein by reference. The preparation of the catalyst precursor takes place by displacement of p-cymene from the [(p-cymene)(Imes)RuCl$_2$]$_2$ species, which is prepared by the deprotonation of the imidazolium salt to form the 1,3-dimesitylimidazol-2-ylidene. The p-cymene complex is then formed and exchanged with t-butylacetylene to form the vinylidene complex. This can then undergo metathesis with the requisite carbene to produce the active species, RuCl$_2$(Imes)(=CH$_2$).

The following structure NHC—X$^2$—Y indicates generically the protected form of an N-Heterocyclic Carbene (NHC).

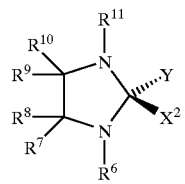

It is also envisioned that the protected NHC—X$^2$—Y may be of an unsaturated variety, such as

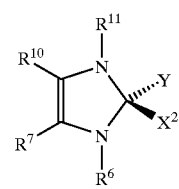

wherein R$^6$, R$^7$, R$^8$, R$^9$, R$^{10}$ and R$^{11}$ are as previously defined.

As shown in Schemes 6a and 6b, the approach taken in this invention relates to the thermal generation of a NHC from a stable (protected) NHC derivative with release of a quantity of X$^2$—Y.

SCHEME 6a

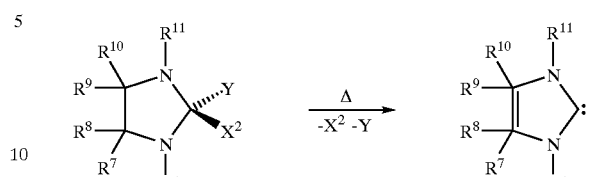

SCHEME 6b

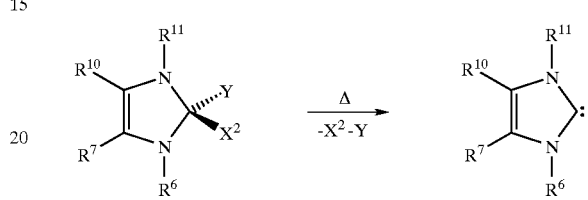

One of the most preferred methods to generate a reactive NHC is to employ a stable carbene precursor where the X$^2$—Y compound is also a reactive NHC, as shown in Schemes 7a and 7b:

SCHEME 7a

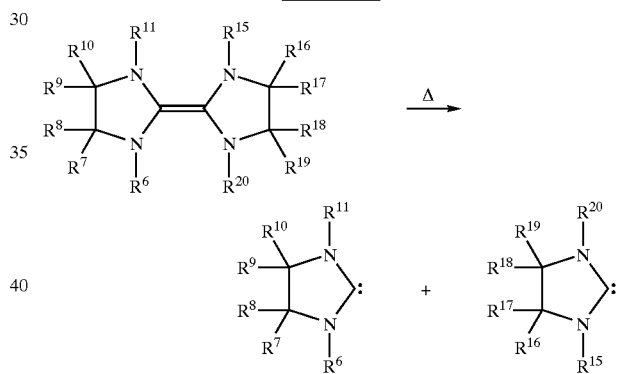

and

SCHEME 7b

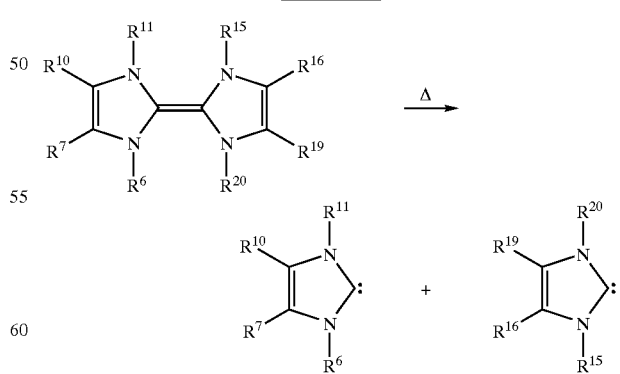

wherein R$^6$, R$^7$, R$^8$, R$^9$, R$^{10}$ and R$^{11}$ are as previously defined and wherein R$^{15}$, R$^{16}$, R$^{17}$, R$^{18}$, R$^{19}$ and R$^{20}$ is independently selected from the group consisting of the moieties in which R$^6$, R$^7$, R$^8$, R$^9$, R$^{10}$ and R$^{11}$ may be selected from.

The first derivative investigated was 1,3-dimesityltrichloromethylimidazoline (s-ImesCHCl$_3$) (I), i.e.,

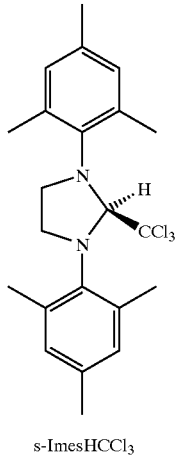

s-ImesHCCl$_3$ where $R^6$ and $R^{11}$=2,4,6-trimethylphenyl and $R^7$, $R^8$, $R^9$, and $R^{10}$=H and $X^2$=H and Y=CCl$_3$ The carbene generated from (I) exists solely as a monomeric species and has no tendency to dimerize under normal conditions. The monomeric nature of the carbene makes it suitable for in-situ generation and reaction with a transition metal containing species.

The 1,3-dimesityltrichloromethylimidazoline starting material can be synthesized by generating the 1,3-dimesityldihydroimidazoline by deprotonation using bases, i.e., potassium hydride (KH), lithium diisopropylamide (LiN(CHMe$_2$)$_2$ or LDA), potassium bis(trimethylsilyl)amide (KN(SiMe$_3$)$_2$), sodium methoxide (NaOMe), and potassium tert-butoxide (KOBu$^t$), and reacting the NHC formed with chloroform in hexane at room temperature. Alternatively and as disclosed in U.S. Pat. No. 4,161,528, the contents of which are incorporated herein by reference, compound I may be generated from the appropriate aniline, dibromoethane, and chloral. Alternatively, the reaction of the ether s-Imes(H)(OCMe$_3$), formed by the action of KOCMe$_3$ on the imidazolium chloride salt (S-ImesHCl), with excess chloroform (CHCl$_3$) in refluxing mixture of chloroform and hexane leads to generation of 1,3-dimesityltrichloromethylimidazoline.

SCHEME 8

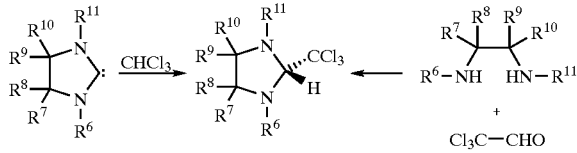

Likewise, the dimethylamine protected forms of imidazolines can be generated from the reaction of equimolar portions of the appropriate diamine and tris(dimethylamino)methane (CH(NMe$_2$)$_3$)or tert-butoxy(bisdimethylamino)methane (CH(NMe$_2$)$_2$OBu$^t$:

SCHEME 9

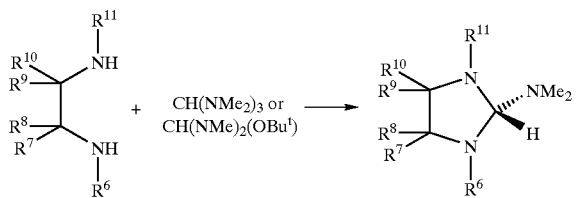

The family of compounds for use in the invention are of the general formula, NHC—$X^2$—Y, that when heated to the appropriate temperature or provided with enough energy generate the free N-heterocyclic carbene and release the $X^2$—Y moiety.

In the above structures, $X^2$ is preferably H but can also be Si, Sn, Li, Na, MgX$^3$ (wherein $X^3$ is any halogen), and acyl and Y may be selected from the group consisting of CCl$_3$; CH$_2$SO$_2$Ph; C$_6$F$_5$; OR$^{21}$; and N(R$^{22}$)(R$^{23}$), wherein $R^{21}$ is selected from the group consisting of Me, C$_2$H$_5$, i-C$_3$H$_7$, CH$_2$CMe$_3$, CMe$_3$, C$_6$H$_{11}$ (cyclohexyl), CH$_2$Ph, CH$_2$norbornyl, CH$_2$norbornenyl, C$_6$H$_5$, 2,4,6-(CH$_3$)$_3$C$_6$H$_2$ (mesityl), 2,6-i-Pr$_2$C$_6$H$_2$, 4-Me—C$_6$H$_4$ (tolyl), 4-Cl—C$_6$H$_4$; and wherein $R^{22}$ and $R^{23}$ are independently selected from the group consisting of Me, C$_2$H$_5$, i-C$_3$H$_7$, CH$_2$CMe$_3$, CMe$_3$, C$_6$H$_{11}$ (cyclohexyl), CH$_2$Ph, CH$_2$norbornyl, CH$_2$norbornenyl, C$_6$H$_5$, 2,4,6-(CH$_3$)$_3$C$_6$H$_2$ (mesityl), 2,6-i-Pr$_2$C$_6$H$_2$, 4-Me—C$_6$H$_4$ (tolyl), 4-Cl—C$_6$H$_4$).

In preferred embodiments of the NHC—$X^2$—Y, $R^7$, $R^8$, $R^9$ and $R^{10}$ are each independently selected from the group consisting of hydrogen, methyl, aralkyl, and aryl and $R^6$ and $R^{11}$ are each independently selected from the group consisting of substituted or unsubstituted C$_1$–C$_{10}$ alkyl, C$_1$–C$_{10}$ cycloalkyl, C$_2$–C$_{10}$ alkenyl, aralkyl, and aryl. In even more preferred embodiments, the $R^7$, $R^8$, $R^9$ and $R^{10}$ are each hydrogen and $R^6$ and $R^{11}$ substituents are selected from the group consisting of phenyl, methyl, isopropyl, tert-butyl, neopentyl, or benzyl, each optionally substituted with one or more moieties selected from the group consisting of C$_1$–C$_5$ alkyl, C$_1$–C$_5$ alkoxy, phenyl, and a functional group. In especially preferred embodiments, $R^6$ and $R^{11}$ are phenyl optionally substituted with one or more moieties independently selected from the group consisting of chloride, bromide, iodide, fluoride, —NO$_2$, —NMe$_2$, methyl, methoxy, and phenyl.

In the more preferred embodiments, $R^6$ and $R^{11}$ are either substituted or unsubstituted aryl. Without being bound by theory, it is believed that the bulkier $R^6$ and $R^{11}$ groups result in initiators with improved characteristics such as thermal and oxidative stability. In the especially preferred embodiments, $R^6$ and $R^{11}$ are the same and each is independently of the formula:

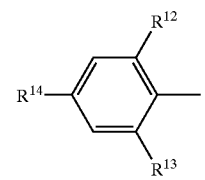

wherein $R^{12}$, $R^{13}$, and $R^{14}$ are independently hydrogen, C$_1$–C$_{10}$ alkyl, C$_1$–C$_{10}$ alkoxy, aryl, or a functional group selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen. In especially preferred embodiments, $R^{12}$, $R^{13}$, and $R^{14}$ are each independently selected from the group consisting of hydrogen, methyl, ethyl, propyl, isopropyl, hydroxyl, and halogen. In the most preferred embodiments, $R^{12}$, $R^{13}$, and $R^{14}$ are the same and are each methyl.

In another embodiment, any or all of the groups, $R^7$, $R^8$, $R^9$ and $R^{10}$, if present, may be linked to form an substituted or unsubstituted, saturated or unsaturated ring structure. In addition, $R^6$ and $R^{11}$ may be linked. The unsaturated ring structure can be aromatic or formed of discrete carbon-carbon single and double bonds. Examples of such ringed species include:

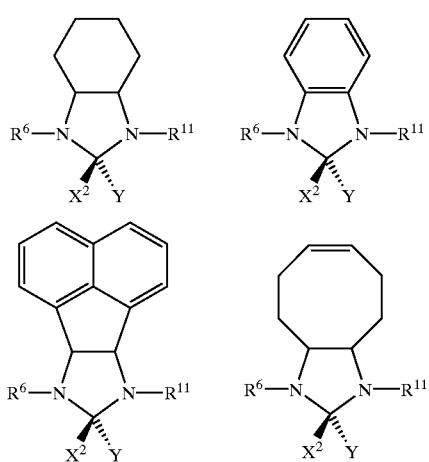
Examples of the most preferred embodiments for use in the invention include:
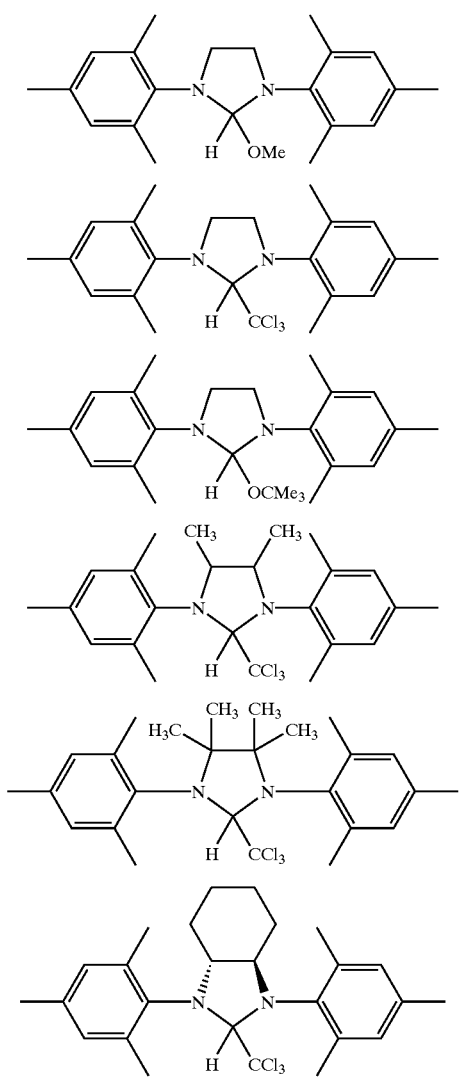
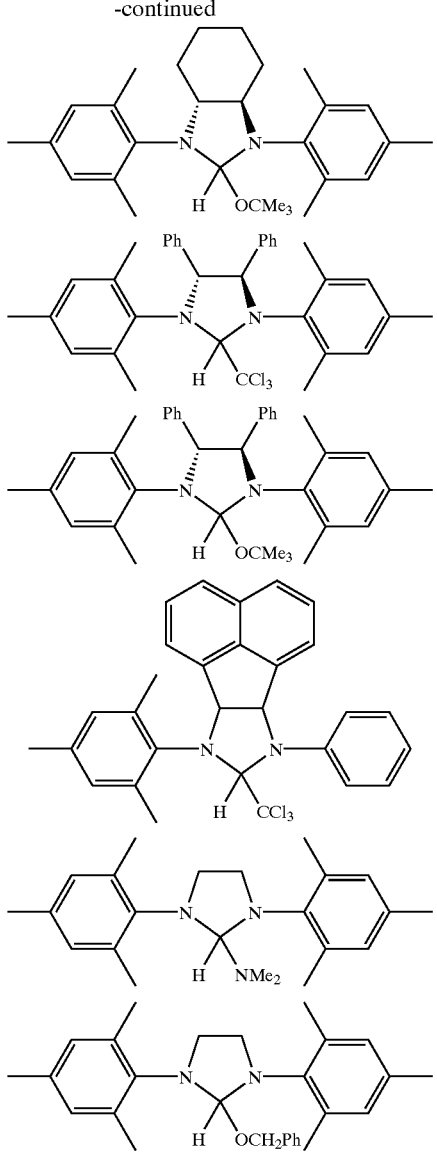
Examples of such di-carbene species, where $X^2$—Y is an NHC, are
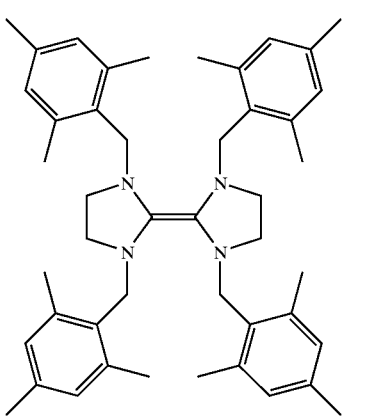

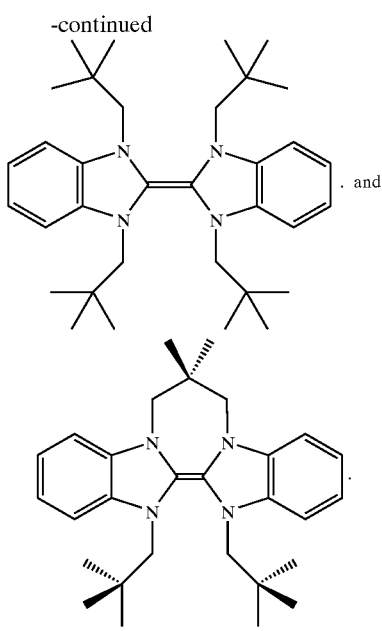

In the case of the tetraaminoethylene complexes, the strength of the carbon-carbon double bond (or carbene stability versus dimerization) is a factor used to gauge its usefulness as a NHC source.

Specific examples of the NHC—$X^2$—Y species are 1,3-dimesityl-2-methoxy-imidazolidine, 1,3-dimesityl-2-ethoxy-imidazolidine, 1,3-dimesityl-2-tert-butoxy-imidazolidine, 1,3-dimesityl-2-benzyloxy-imidazolidine, 1,3-diphenyl-2-(trichloromethyl)imidazolidine, 1,3-bis(3-chlorophenyl)-2-(trichloromethyl)imidazolidine, 1,3-bis(4-methylphenyl)-2-(trichloromethyl)imidazolidine, 1,3-bis(4-fluorophenyl)-2-(trichloromethyl)imidazolidine, 1,3-bis(3-methylphenyl)-2-(trichloromethyl)imidazolidine, 1,3-bis(4-chlorophenyl)-2-(trichloromethyl)imidazolidine, 1,3-bis(4-bromophenyl)-2-(trichloromethyl)imidazolidine, 1,3-bis(4-iodophenyl)-2-(trichloromethyl)imidazolidine, 1,3-bis(4-methoxyphenyl)-2-(trichloromethyl)imidazolidine, 1,3-bis(4-ethoxyphenyl)-2-(trichloromethyl)imidazolidine, 1,3-bis(4-ethylphenyl)-2-(trichloromethyl)imidazolidine, 1,3-bis(4-nitrophenyl)-2-(trichloromethyl)imidazolidine, 1,3-bis(3,4-dimethylphenyl)-2-(trichloromethyl)imidazolidine, 1,3-bis(3,5-dichlorophenyl)-2-(trichloromethyl) imidazolidine, 1,3-bis(3,5-dimethylphenyl)-2-(trichloromethyl imidazolidine, 1-(4-chlorophenyl)-3-phenyl-2-(trichloromethyl)imidazolidine, 1,3-bis(4-fluorophenyl)-2-(trichloromethyl)imidazolidine, 1-(4-methoxyphenyl)-3-phenyl-2-(trichloromethyl imidazolidine, 2-(trichloromethyl)-1,3-bis(2,6-dimethyl-4-tert-butylphenyl)imidazolidine, 2-(trichloromethyl)-1,3-bis(2,6-diisopropylphenyl)imidazolidine, 1,3-dimesityl-2-dimethylamino-imidazolidine, 1-(1,3-dimesityl-2-imidazolidinyl)piperidine, 1,3-dimesityl-2-(trichloromethyl)imidazolidine, and 4-(1,3-dimesityl-2-imidazolidinyl)-morpholine.

The temperature range for the deprotection of the NHC—$X^2$—Y compound is from about −50 to about 250° C.; preferably in the range of about 0 to about 200° C.; more preferably, in the range of about 50 to about 150° C.; and most preferably in the range of about 75 to about 125° C. Both polar and apolar solvents can be employed as suitable medium for the thermal deprotection of the NHC—$X^2$—Y compound, although solventless polymerization is also possible. The use of a particular solvent will depend on both the stability of the stabilized NHC—$X^2$—Y, and also on the solubility of the initial metal derivative, as well as the final metal initiator. Suitable solvents will include hexane, heptane, octane, nonane, decane, decalin, benzene, toluene, ethylbenzene, ortho-xylene, meta-xylene, and para-xylene, mesitylene, chlorobenzene, dichlorobenzene, bromobenzene, dibromobenzene, ethanol, propanol, butanol, pentanol, and hexanol. Suitable polycyclic monomers will include norbornene, methyl norbornene, butylnorbornene, hexylnorbornene, decylnorbornene, dicyclopentadiene, tricyclopentadiene, methyltetracyclododecene, and tetracyclododecene together with their cyclopentadiene congeners. The NHC may be generated either as a solution or in the presence of a ruthenium or osmium complex.

The preferred method for deprotecting the NHC precursor is by supplying energy in the form of thermal energy, i.e., heat; however, laser, electron beam radiation, gamma radiation, plasma, sound, ultra-violet (UV), or microwave radiation can also be used.

Scheme 10 depicts the thermal activation of an unsaturated NHC precursor and a ligand exchange to form a more active metathesis initiator:

SCHEME 10

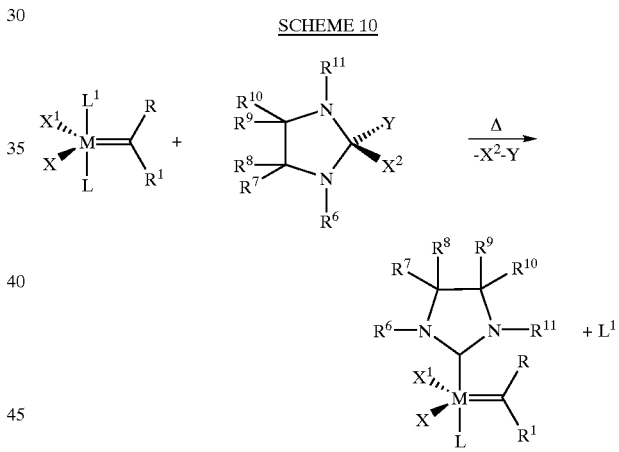

This exchange may be performed in solvent or monomer. In general, the selected NHC should be more basic than the leaving group, i.e. L or $L^1$. Thus, for example, a saturated or unsaturated NHC is expected to be able to displace one phosphine (in solvent or reactive monomer), ether, or imidazolidine (where $R^{50a}$, $R^{50b}$, $R^{50c}$, and $R^{50d}$ may be selected from any of the groups in which $R^6$ and $R^{11}$ may be selected from. Preferably, in these examples, $R^{50a}$, $R^{50b}$, $R^{50c}$, and $R^{50d}$ are each independently alkyl or aralkyl (e.g., benzyl)) from any of the following exemplary initiator species:

-continued

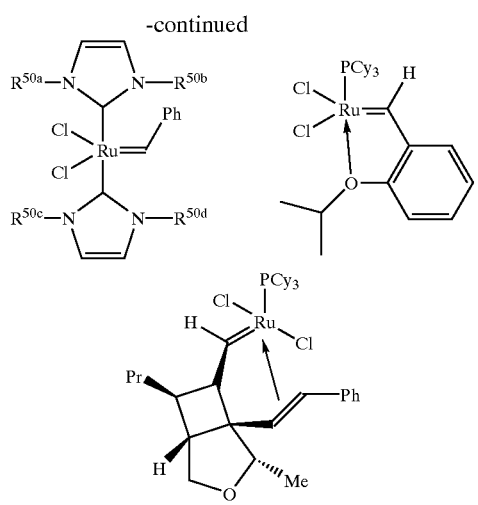

Preferably the initiators are selected from group 8 alkylidene species or cumulated species. In addition, the initiators may be tetra-coordinated, penta-coordinated, or hexa-coordinated. Examples of hexa-coordinated initiators can be seen in U.S. patent application Ser. No. 10/017,489, filed Dec. 14, 2001, entitled "Hexacoordinated Ruthenium or Osmium Metal Carbene Metathesis Catalysts," the contents of which are incorporated herein by reference.

For example, the pentacoordinated complex may lose the L or $L^1$ ligand to form a metathesis active tetracoordinated species as depicted below in Scheme 11:

SCHEME 11

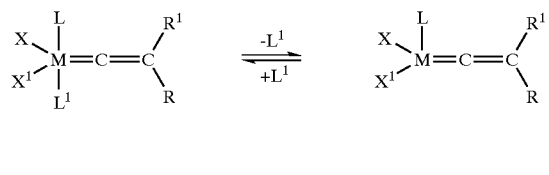

As shown in Scheme 11, the L or $L^1$ ligand may also attach to a tetracoordinated species to form the pentacoordinated complex.

The tetracoordinated species may then initiate polymerization when in the presence of an olefin, as shown in Scheme 12, or may form the NHC based pentacoordinated complex when in the presence of a protected NHC that has become deprotected, or lost $X^2$ and Y, to form the free NHC-ligand or carbene (Scheme 13):

SCHEME 12

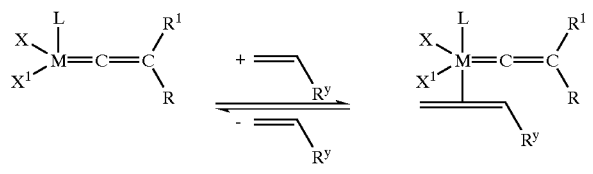

SCHEME 13

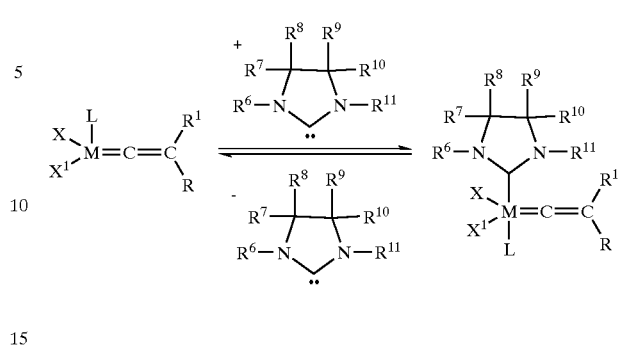

The pentacoordinated NHC complex may then lose the L ligand to form the metathesis active tetracoordinated NHC species (Scheme 14):

SCHEME 14

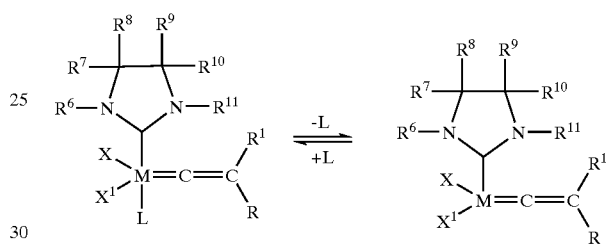

The tetracoordinated NHC species may then initiate polymerization when in the presence of an olefin, as shown in Scheme 15:

SCHEME 15

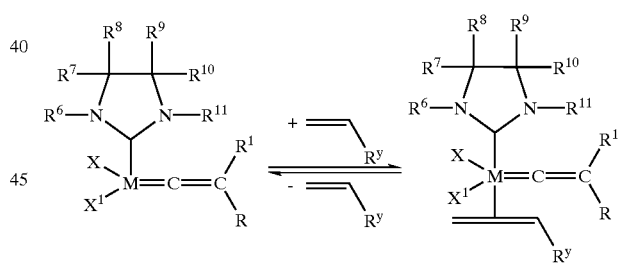

Alternatively, a tetracoordinated species in the presence of a protected NHC can by ligand exchange form the NHC tetracoordinated species and then initiate polymerization when in the presence of an olefin and energy without having to form an intermediate pentacoordinated complex.

More preferably, the initiators are of the following general formulas where the leaving group, i.e. L or $L^1$, is replaceable by an NHC.

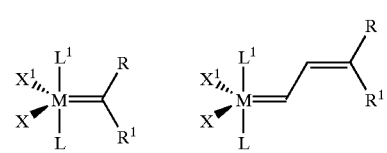

-continued

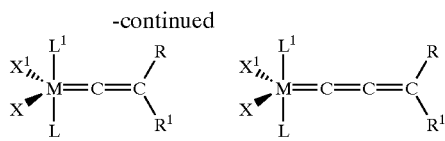

In the above general formulas for metathesis catalysts:

M is preferably ruthenium or osmium;

X and $X^1$ are each independently any anionic ligand, preferably Cl, Br, I, $CH_3CO_2$ and $CF_3CO_2$;

L and $L^1$ are each independently any neutral electron donor ligand, for example a Lewis base, where either L or $L^1$ may be substituted by the generated NHC ligand; and, R and $R^1$ are preferably each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl, $C_1$–$C_{20}$ alkylsulfinyl and silyl. Optionally, each of the R and $R^1$ substituent group may be substituted with one or more moieties selected from the group consisting of $C_1$–$C_{10}$ alkyl, $C_1$–$C_{10}$ alkoxy, and aryl which in turn may each be further substituted with one or more groups selected from a halogen, a $C_1$–$C_5$ alkyl, $C_1$–$C_5$ alkoxy, and phenyl. Furthermore, any of the catalyst ligands may further include one or more functional groups. Examples of suitable functional groups include but are not limited to: alcohol, sulfonic acid, phosphine, thiol, thioether, ketone, aldehyde, ester, ether, amine, imine, amide, imide, imido, nitro, carboxylic acid, disulfide, carbonate, isocyanate, carbodiimide, carboalkoxy, carbamate, acetal, ketal, boronate, cyano, cyanohydrin, hydrazine, oxime, hydrazide, enamine, sulfone, sulfide, sulfenyl, and halogen.

In preferred embodiments of these catalysts, the R substituent is hydrogen and the $R^1$ substituent is selected from the group consisting of $C_1$–$C_{20}$ alkyl, $C_2$–$C_{20}$ alkenyl, and aryl. In even more preferred embodiments, the $R^1$ substituent is phenyl, methyl, vinyl, isopropyl, or tert-butyl, each optionally substituted with one or more moieties selected from the group consisting of $C_1$–$C_5$ alkyl, $C_1$–$C_5$ alkoxy, phenyl, and a functional group. In especially preferred embodiments, $R^1$ is tert-butyl or phenyl or vinyl optionally substituted with one or more moieties selected from the group consisting of chloride, bromide, iodide, fluoride, —$NO_2$, —$NMe_2$, methyl, methoxy, and phenyl.

In preferred embodiments of these catalysts, X and $X^1$ are each independently hydrogen, halide, or one of the following groups: $C_1$–$C_{20}$ alkyl, aryl, $C_1$–$C_{20}$ alkoxide, aryloxide, $C_3$–$C_{20}$ alkyldiketonate, aryldiketonate, $C_1$–$C_{20}$ carboxylate, arylsulfonate, $C_1$–$C_{20}$ alkylsulfonate, $C_1$–$C_{20}$ alkylthio, $C_1$–$C_{20}$ alkylsulfonyl, or $C_1$–$C_{20}$ alkylsulfinyl. Optionally, X and $X^1$ may be substituted with one or more moieties selected from the group consisting of $C_1$–$C_{10}$ alkyl, $C_1$–$C_{10}$ alkoxy, and aryl, which in turn may each be further, substituted with one or more groups selected from halogen, $C_1$–$C_5$ alkyl, $C_1$–$C_5$ alkoxy, and phenyl. In more preferred embodiments, X and $X^1$ are halide, benzoate, $C_1$–$C_5$ carboxylate, $C_1$–$C_5$ alkyl, phenoxy, $C_1$–$C_5$ alkoxy, $C_1$–$C_5$ alkylthio, aryl, and $C_1$–$C_5$ alkyl sulfonate. In even more preferred embodiments, X and $X^1$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethanesulfonate. In the most preferred embodiments, X and $X^1$ are each chloride.

In preferred embodiments of these catalysts, L and $L^1$ are each independently selected from the group consisting of phosphine, sulfonated phosphine, phosphite, phosphinite, phosphonite, arsine, stibine, ether, amine, amide, imine, sulfoxide, carboxyl, nitrosyl, pyridine, thioether and heterocyclic carbene. In more preferred embodiments, L and $L^1$ are phosphines of the formula $PR^3R^4R^5$, where $R^3$, $R^4$, and $R^5$ are each independently aryl or $C_1$–$C_{10}$ alkyl, particularly primary alkyl, secondary alkyl or cycloalkyl.

In the most preferred embodiments, L and $L^1$ are each selected from the group consisting of P(cyclohexyl)$_3$, P(cyclopentyl)$_3$, P(isopropyl)$_3$, P(sec-butyl), and P(phenyl)$_3$.

Preferred initiators useful with thermal activation NHC precursors may be selected from the following compounds (designated by their approximate molecular weight):

Ru 575
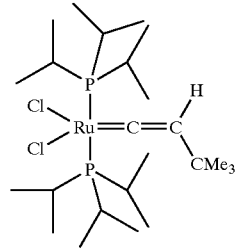

Ru 595
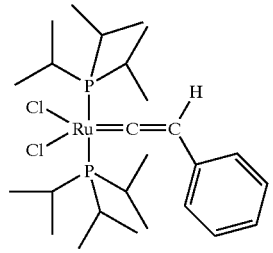

Ru 716
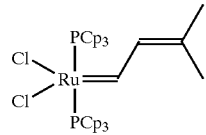

Ru 731
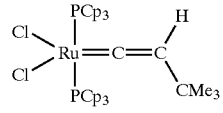

Ru 751
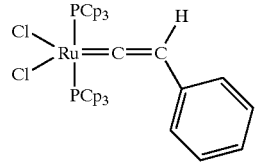

Ru 779
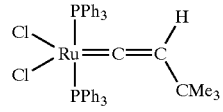

Ru 799
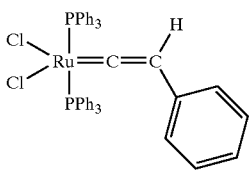

Ru 801
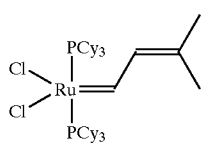

Ru 815
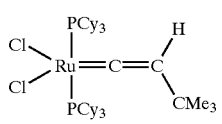

Ru 823
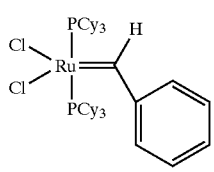

Ru 835
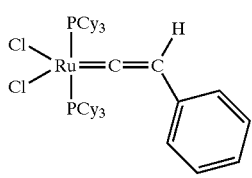

Ru 801(B)
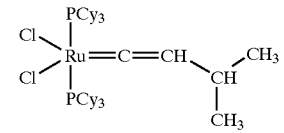

Ru 801(C)
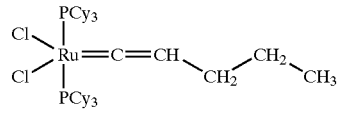

Ru 815(B)
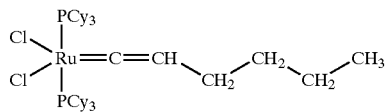

Ru 843
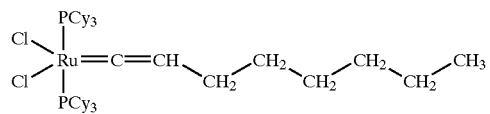

Ru 831
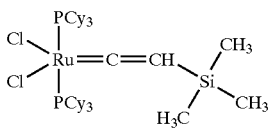

A preferred examople of a Ru or Os initiators to be admixed with NHC-$X^2$-Y species is the following:

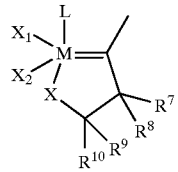

wherein M=Ru or Os;

$X_1$ and $X_2$ represent any anionic ligand independently selected from the group consisting of chloride (Cl)), bromide (Br), iodide (I), thiocyanate (SCN), cyanide (CN), carboxylate (OC(O)R), trifluoroacetate (OC(O)CF$_3$), triflate (O$_3$SCF$_3$), triflimide (N(SO$_2$CF$_3$)$_2$), acetylacetonate (acac), alkoxide (RO), aryloxide (ArO), and tosylate (O$_3$SC$_6$H$_4$CH$_3$);

X is functional group capable of binding to the metal center and is also attached to the alkylidene portion ("site of initiation" and subsequent "catalytic" ring-opening of strained rings) of the initiator through the carbon skeleton; and wherein X is selected from the group consisting of alkoxy (—OR), thiooxy (—SR), phosphine (—PR$_2$), phosphine (—P(O)R$_2$), amido (—NR$_2$), arsine (—AsR$_2$), stibene (—SbR$_2$), alkene (—CR=CR$_2$), alkyne (—CCR), carboxylate (—OC(O)R), acetate (—C(O)OR), sulfinyl (—S(O)R), sulfonyl (—S(O)R), sulfonate (—OS(O)$_2$R), keto (—C(O)R), aldehyde (—C(O)H), and imido (—C=N—R or C—N=R); and L is a donor of electrons, wherein the electron donor may be anionic, neutral, radical, or cationic. Typical electron donors are neutral, e.g., imidazole carbenes, pyridines, ethers, amines, phosphines, phosphinites, phosphonites, and phosphites. Phosphines are the preferred ligands in this invention. Trialkyl phosphines are preferred over triarylphosphines. More preferred phosphines are those containing at least one secondary or alkyl or a cycloalkyl group, and the most preferred embodiment the alkyl groups are either isopropyl, isobutyl, sec-butyl, neopentyl, neophyl, cyclopentyl, or cyclohexyl, i.e., triisopropylphosphine or tricyclohexylphosphine. L is selected to be a weaker base than the NHC generated from NHC—$X^2$—Y.

R, $R^7$, $R^8$, $R^9$ and $R^{10}$ are as previously defined. Preferably, R, $R^7$, $R^8$, $R^9$, and $R^{10}$ are independently selected from the group consisting of hydrogen or hydrocarbyl or silyl groups from the group consisting of C$_1$–C$_{20}$ alkyl, C$_2$–C$_{20}$. More preferably, R, $R^7$, $R^8$, $R^9$, and $R^{10}$ are independently selected from hydrogen, hydrocarbyl, polycyclic, fused polycyclic or silyl. When the carbon atoms to which $R^7$, $R^8$, $R^9$, and $R^{10}$ are attached form vinylic or aromatic bonds only two of these groups are required. Representative polycyclic and fused polycyclic ring structures, such as cyclopentyl, cyclohexyl, benzene, or naphthalene.

The following structures are examples of Ru or Os initiators to be admixed with NHC—$X^2$—Y species.

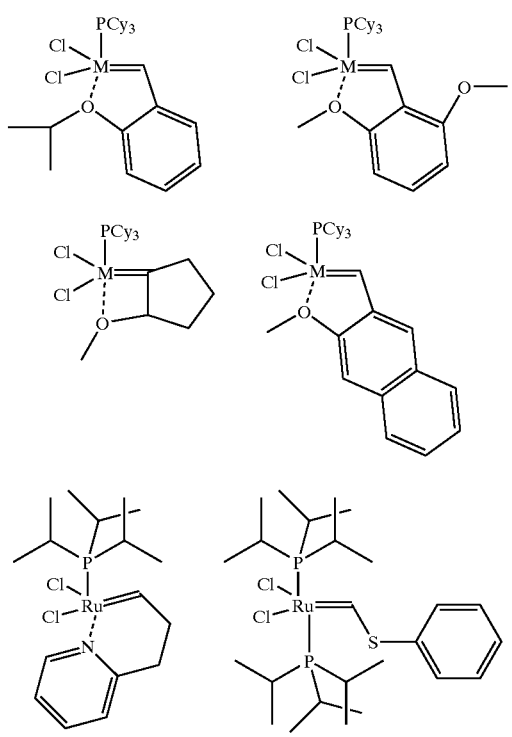

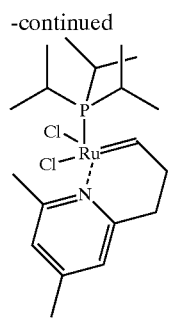

The complexes $RuX_2(PPh_3)_3$ (X=Cl, Br) react with excess $HC\equiv CCMe_3$ in benzene over 24 h at room temperature to give vinylidene complexes of the formula $RuX_2(PPh_3)_2(=C=CHCMe_3)$. In related chemistry and catalysis, it has been demonstrated that vinylidene ruthenium complexes of the formula $RuX_2(PR_3)_2(=C=CHCMe_3)$ (R=Ph, i-Pr, Cy (cyclohexyl) and Cp (cyclopentyl)) are good catalyst precursors for the ROMP or norbornene derivatives. These species were discussed as possessing much lower catalysts efficiency as compared to the prevailing Grubbs' initiator. The vinylidene complex with R=Ph was prepared by the reaction of $RuCl_2(PPh_3)_3$ with tert-butylacetylene; ligand exchange was used to obtained the i-Pr, Cy and Cp complexes. In addition, various $RuX_2(PR_3)_2(=C=C(H)R)$ species can be prepared in high yield through heating a toluene solution of $[RuCl_2(p\text{-cymene})]_2$, phosphine (2 equiv./Ru), and alkyne (1 equivalent/Ru) at 80° C. to selectively form the corresponding vinylidene species.

In contrast, the invention also proposes that the in-situ generation and thermal deprotection of the NHC be used as a method to generate NHC containing ruthenium alkylidene derivatives under similar conditions to those described above, i.e.,

SCHEME 16

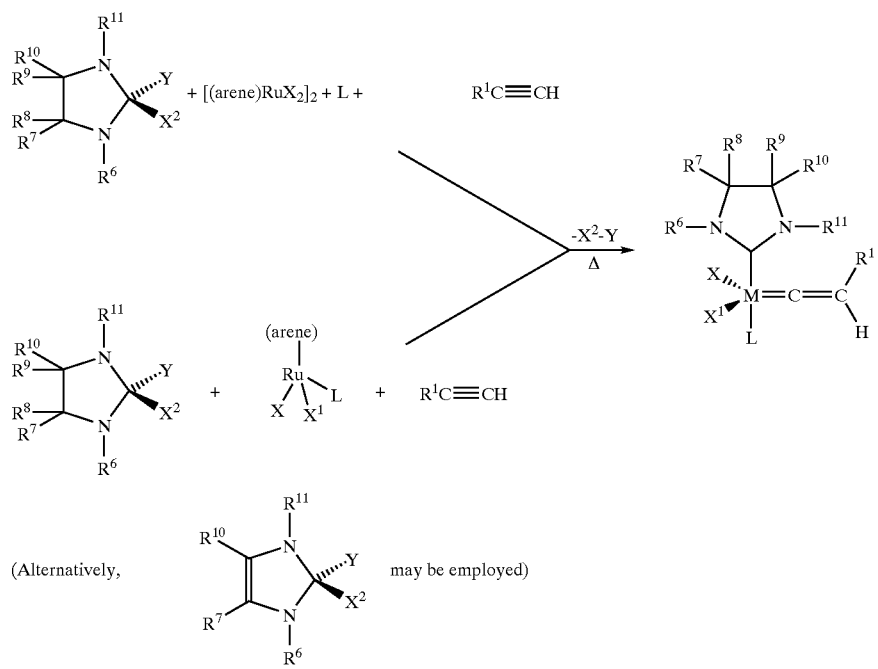

The neutral electron donor (L) employed in the above reaction may be selected from PMe$_3$, PPhMe$_2$, PEt$_3$, P(OMe)$_3$, PPh$_2$Me, PPh$_2$Et, PBz$_3$, PCyPh$_2$, P-i-Bu$_3$, P(4-CH$_3$OC$_6$H$_4$)$_3$, P(4-CH$_3$OC$_6$H$_4$)$_3$, P(4-FC$_6$H$_4$)$_3$, P(4-ClC$_6$H$_4$)$_3$, P(4-CF$_3$C$_6$H$_4$)$_3$, PCy$_3$, PCp$_3$, PCy$_2$Ph, P(OPh)$_3$, P-i-Pr$_3$, and PPh$_3$. The preferred L would be selected from triphenylphosphine, triisopropylphosphine, tricyclohexylphosphine, and tricyclopentylphosphine (PCp$_3$). Arene=benzene containing hydrocarbyl, i.e., benzene, p-cymene, xylene, and toluene. The preferred arene is p-cymene.

U.S. Pat. No. 6,107,420, the contents of which are incorporated herein by reference, describes the synthesis of numerous RuX$_2$(PR$_3$)$_2$(=C=C(H)R) species and how such species could be thermally initiated in the presence of cyclic olefins. In this same issued patent, similar vinylidene derivatives as those described in the above scheme, i.e., RuCl$_2$(Imes)(PCy$_3$)(=C=C(H)—CMe$_3$)) have been disclosed.

Scheme 17 below additionally employs the thermally deprotectable NHC to prepare a NHC in situ with one equivalent of a suitable Lewis base and an α,α-dihalosubstituted toluene, i.e., and 1-chloropentane; ethers such as THF and diethylether; aromatic solvents such as benzene, xylene, toluene, mesitylene, chlorobenzene, and o-dichlorobenzene; primary, secondary and tertiary alcohols, and halocarbon solvents such as Freon® 112; and mixtures thereof. Preferred solvents include benzene, fluorobenzene, o-difluorobenzene, p-difluorobenzene, pentafluorobenzene, hexafluorobenzene, o-dichlorobenzene, chlorobenzene, toluene, o-, m-, and p-xylenes, mesitylene, cyclohexane, THF, dichloromethane, liquid rubbers, and liquid antioxidants. More preferred solvents include secondary and tertiary alcohols which may be compounds of the formula HC(R$^{40}$)(R$^{41}$)OH or R$^{40}$C(R$^{41}$)(R$^{42}$)OH, wherein R$^{40}$, R$^{41}$, and R$^{42}$ are each independently of the others C$_1$–C$_{20}$ alkyl, or C$_4$–C$_{12}$ cycloalkyl which is unsubstituted or substituted by C$_1$–C$_6$ alkyl, C$_1$–C$_6$ haloalkyl, —NO2 or by C$_1$–C$_6$ alkoxy, or C$_6$–C$_{16}$ aryl which is unsubstituted or substituted by C$_1$–C$_6$ alkyl, C$_1$–C$_6$ haloalkyl, —NO2 or by C$_1$–C$_6$ alkoxy, or C$_7$–C$_{16}$ arylalkyl which is unsubstituted or substituted by C$_1$–C$_6$ alkyl, C$_1$–C$_6$ haloalkyl, —NO2 or by C$_1$–C$_6$ alkoxy; or the radicals R$^{40}$ and R$^{41}$ together are tetra- or penta-methylene which is

SCHEME 17

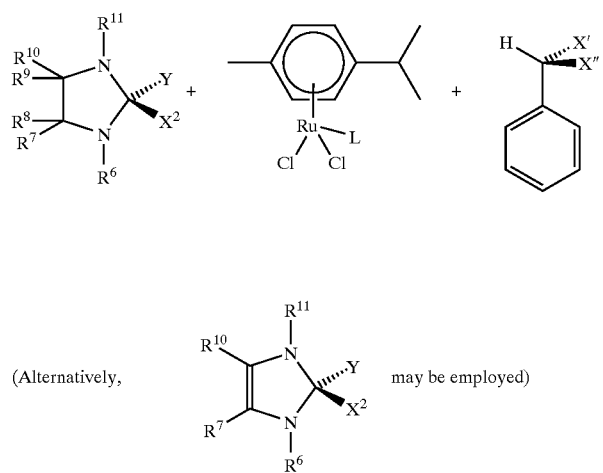

(Alternatively, [structure] may be employed)

The neutral electron donor (L) employed in the above reaction may be selected from PMe$_3$, PPhMe$_2$, PEt$_3$, P(OMe)$_3$, PPh$_2$Me, PPh$_2$Et, PBz$_3$, PCyPh$_2$, P-i-Bu$_3$, P(4-CH$_3$OC$_6$H$_4$)$_3$, P(4-CH$_3$OC$_6$H$_4$)$_3$, P(4-FC$_6$H$_4$)$_3$, P(4-ClC$_6$H$_4$)$_3$, P(4-CF$_3$C$_6$H$_4$)$_3$, PCy$_3$, PCp$_3$, PCy$_2$Ph, P(OPh)$_3$, P-i-Pr$_3$, and PPh$_3$. The preferred L would be selected from triphenylphosphine (PPh$_3$), tricyclohexylphosphine (PCy$_3$), triisopropylphosphine (P-i-Pr$_3$), and tricyclopentylphosphine (PCp$_3$). X' and X" can be selected from the same group as X and X$^1$ as previously defined.

In addition, Scheme 18 is another route to mixed NHC/PR$_3$ species provided that the appropriate deprotectable NHC and solvent is selected. The NHC may be any previously discussed NHC. The solvents include but are not limited to alkane and cycloalkane solvents such as pentane, hexane, heptane, and cyclohexane; halogenated alkane solvents such as dichloromethane, chloroform, carbon tetrachloride, ethylchloride, 1,1-dichloroethane, 1,2-dichloroethane, 1-chloropropane, 2-chloropropane, 1-chlorobutane, 2-chlorobutane, 1-chloro-2-methylpropane, unsubstituted or substituted by C$_1$–C$_6$ alkyl, C$_1$–C$_6$ haloalkyl, —NO2 or by C$_1$–C$_6$ alkoxy, or tetra- or penta-methylene which is unsubstituted or substituted by C$_1$–C$_6$ alkyl, C$_1$–C$_6$ haloalkyl, —NO2 or by C$_1$–C$_6$ alkoxy and condensed with one or two 1,2-phenylene(s), and R$^{42}$ is as defined above. R$^{40}$, R$^{41}$, and R$^{42}$ are preferably each independently of the others C$_1$–C$_{20}$ alkyl, or C$_4$–C$_{12}$ cycloalkyl which is unsubstituted or substituted by C$_1$–C$_6$ alkyl, C$_1$–C$_6$ haloalkyl, —NO2 or by C$_1$–C$_6$ alkoxy. R$^{40}$, R$^{41}$, and R$^{42}$ are more preferably each independently of the others C$_1$–C$_{20}$ alkyl, or C$_4$–C$_{12}$ cycloalkyl. R$^{40}$, R$^{41}$, and R$^{42}$ are most preferably methyl, ethyl, propyl, isopropyl, butyl, isobutyl and sec-butyl.

SCHEME 18

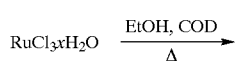

-continued

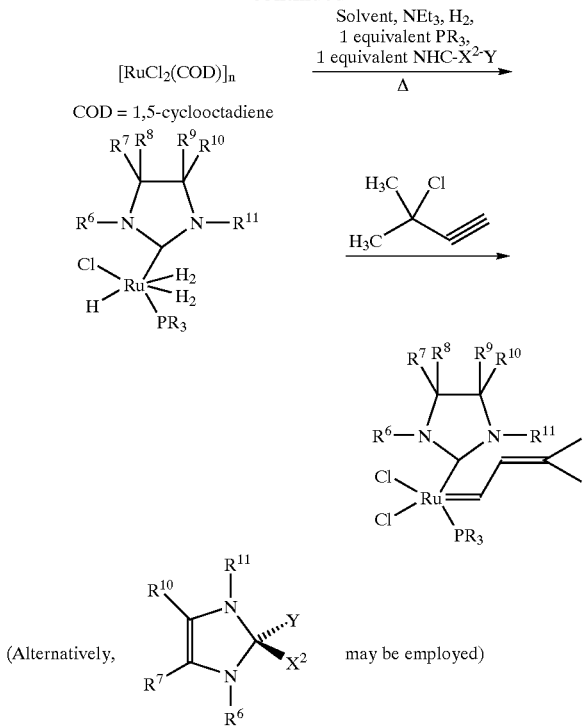

The catalytic activity of phosphine containing ruthenium olefin metathesis initiators can be improved significantly by the addition these thermally deprotected NHC. This is useful in the ring-opening metathesis polymerization (ROMP) of DCPD where the polymerization exotherm exceeds about 200° C., since the protected form of the NHC becomes deprotected during the course of the reaction and, at the end of the polymerization, the NHC can stabilize the ROMP catalyst more effectively at the higher temperatures than can a phosphine. For example, the addition of compound (I) to a mixture of $RuCl_2(PCy_3)_2(=CH-CH=CMe_2)$ enables the ruthenium content to be lowered from the usually employed 7,500:1 (DCPD:Ru (mole ratio)) to a more preferable (40,000:1) while still maintaining excellent conversion (see Examples). Thus, it is possible to get enhanced ROMP activity without having to isolate a discrete NHC containing initiator and in the presence of a liberated phosphine ligand.

The reactivity of the Initiator A type systems can also be modified further through the addition of neutral electron donor ligands, such as triphenylphosphine or triphenylphosphite, thereby enabling the gel and exotherm times to be delayed at lower temperature for longer times. However, once the exothermic reaction has taken place, full conversion would be achieved through in-situ generation of the more active NHC metal carbene metathesis catalysts.

In the following schemes 19–22 any base (proton acceptor) and any acid (proton donor) is suitable. Preferred bases are those having a greater basicity than water. Examples are tertiary amines, metal hydroxides, metal alcoholates and metal phenolates. Preferred bases are triethylamine, 1,8-diazabicyclo[5.4.0]undec-7-ene, KOH, NaOH, KO-tert-butyl and NaO-methyl, especially triethylamine and diazabicyclo[5.4.0]undec-7-ene. Preferred acids are hydrohalic acids. Examples are selected from the group consisting of HF, HCl, HBr, and HI, special preference being given to HCl and HBr.

SCHEME 19

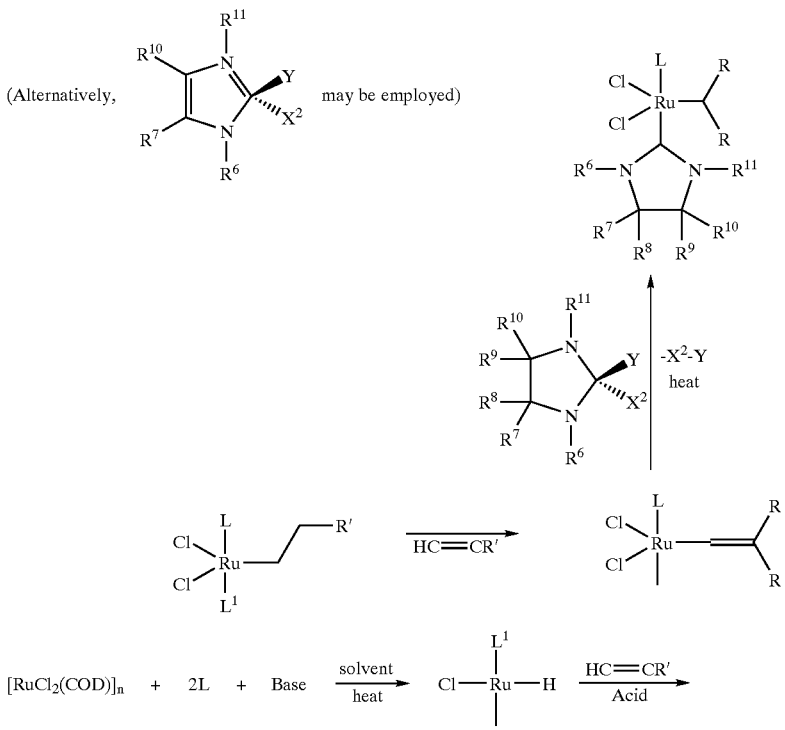

SCHEME 20

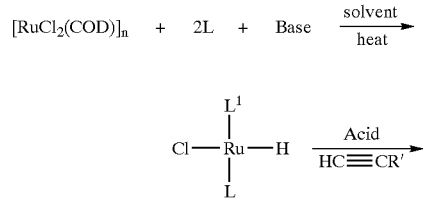
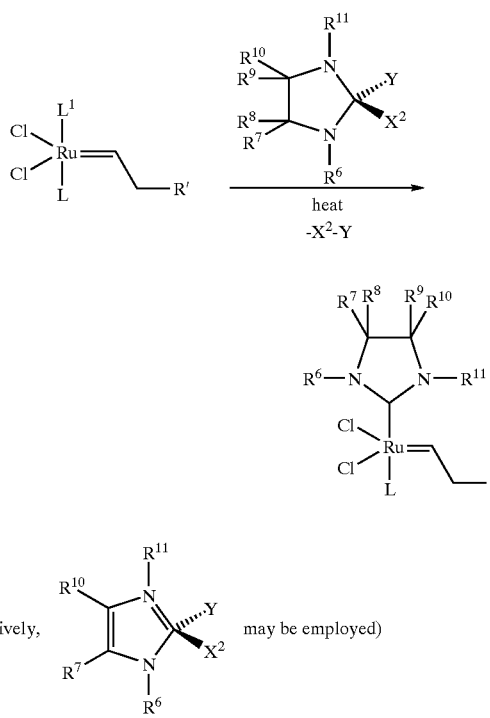

SCHEME 21

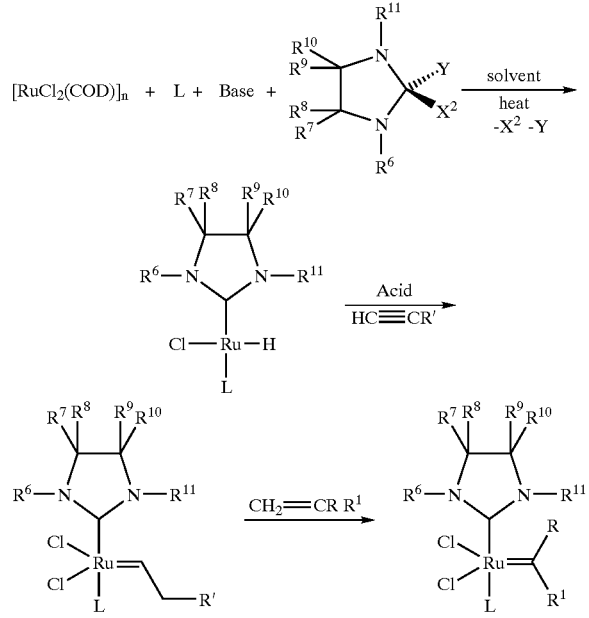

SCHEME 22

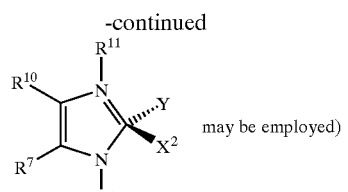
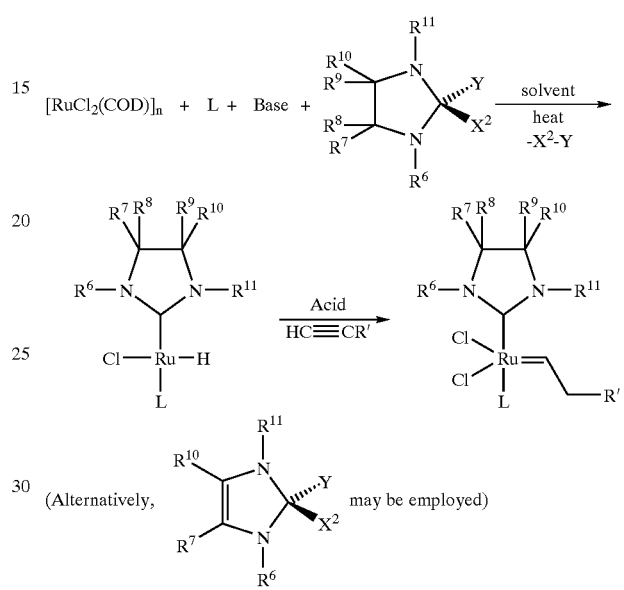

In Schemes 19–22, suitable solvents include but are not limited to alkane and cycloalkane solvents such as pentane, hexane, heptane, and cyclohexane; halogenated alkane solvents such as dichloromethane, chloroform, carbon tetrachloride, ethylchloride, 1,1-dichloroethane, 1,2-dichloroethane, 1-chloropropane, 2-chloropropane, 1-chlorobutane, 2-chlorobutane, 1-chloro-2-methylpropane, and 1-chloropentane; ethers such as THF and diethylether; aromatic solvents such as benzene, xylene, toluene, mesitylene, chlorobenzene, and o-dichlorobenzene; primary, secondary and tertiary alcohols, and halocarbon solvents such as Freon® 112; and mixtures thereof. Preferred solvents include benzene, fluorobenzene, o-difluorobenzene, p-difluorobenzene, pentafluorobenzene, hexafluorobenzene, o-dichlorobenzene, chlorobenzene, toluene, o-, m-, and p-xylenes, mesitylene, cyclohexane, THF, dichloromethane, liquid rubbers, and liquid antioxidants. More preferred solvents include secondary and tertiary alcohols which may be compounds of the formula $HC(R^{40})(R^{41})OH$ or $R^{40}C(R^{41})(R^{42})OH$, wherein $R^{40}$, $R^{41}$, and $R^{42}$ are each independently of the others $C_1$–$C_{20}$ alkyl, or $C_4$–$C_{12}$ cycloalkyl which is unsubstituted or substituted by $C_1$–$C_6$ alkyl, $C_1$–$C_6$ haloalkyl, —NO2 or by $C_1$–$C_6$ alkoxy, or $C_6$–$C_{16}$ aryl which is unsubstituted or substituted by $C_1$–$C_6$ alkyl, $C_1$–$C_6$ haloalkyl, —NO2 or by $C_1$–$C_6$ alkoxy, or $C_7$–$C_{16}$ arylalkyl which is unsubstituted or substituted by $C_1$–$C_6$ alkyl, $C_1$–$C_6$ haloalkyl, —NO2 or by $C_1$–$C_6$ alkoxy; or the radicals $R^{40}$ and $R^{41}$ together are tetra- or penta-methylene which is unsubstituted or substituted by $C_1$–$C_6$ alkyl, $C_1$–$C_6$ haloalkyl, —NO2 or by $C_1$–$C_6$ alkoxy, or tetra- or penta-methylene which is unsubstituted or substituted by $C_1$–$C_6$ alkyl, $C_1$–$C_6$ haloalkyl, —NO2 or by $C_1$–$C_6$ alkoxy and condensed with one or two 1,2-phenylene(s), and $R^{42}$ is as defined above. $R^{40}$, $R^{41}$, and $R^{42}$ are preferably each independently of the others $C_1$-$C_{20}$ alkyl, or $C_4$-$C_{12}$ cycloalkyl which is unsubstituted or substituted by $C_1$-$C_6$ alkyl, $C_1$-$C_6$ haloalkyl, —NO2 or by $C_1$-$C_6$ alkoxy. $R^{40}$, $R^{41}$, and $R^{42}$ are more preferably each independently of the others $C_1$-$C_{20}$ alkyl, or $C_4$-$C_{12}$ cycloalkyl. $R^{40}$, $R^{41}$, and $R^{42}$ are most preferably methyl, ethyl, propyl, isopropyl, butyl, isobutyl and sec-butyl.

In schemes 19–22, L, $L^1$, R, $R^1$, are as previously defined. R' can be selected from any of the groups that R or $R^1$ may be selected from. In addition, the protected NHC—$X^2$—Y can be any protected NHC—$X^2$—Y as previously defined.

Similarly, the invention provides that the addition of the following triazole,

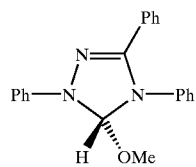

to a mixture of a phosphine based Ru alkylidene in DCPD would allow for a reduced concentration of Ru initiator to be added to the system, since a more active catalyst would be formed by the in-situ elimination of methanol from the methoxide.

Alternatively, any stable carbene may be admixed with an initiator to achieve an improvement in catalyst efficiency, i.e.,

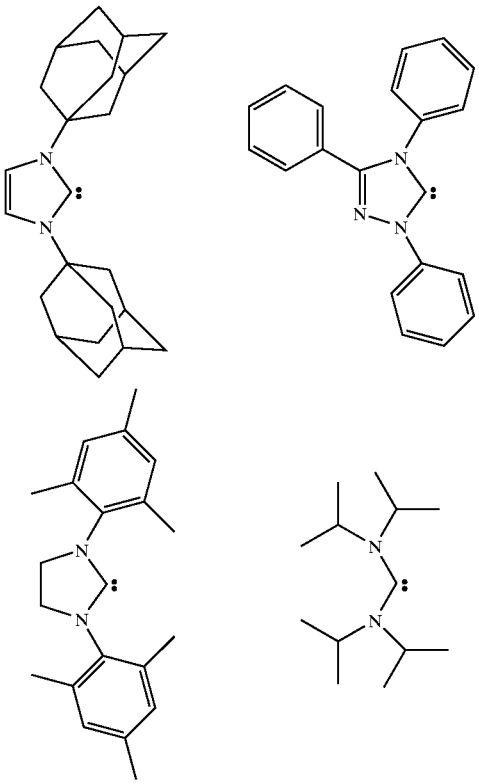

-continued

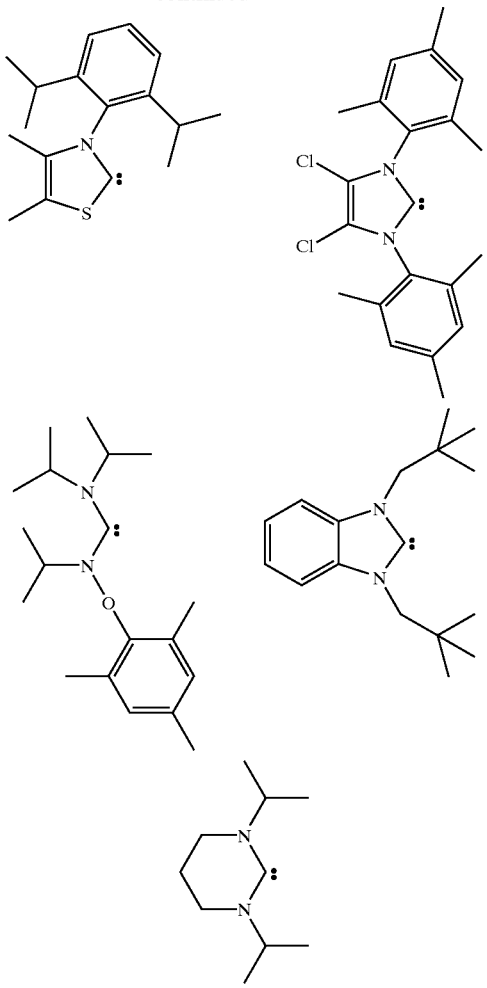

Reaction Thermodynamics

The success of the deprotection of the NHC—$X^2$—Y is in part dependent on the quantity of energy released during the polymerization of cyclic olefin. The faster the energy is released and the more energy released the more likely a critical concentration of NHC will be formed.

For example, the release of ring strain during ring opening metathesis polymerization (ROMP) of dicyclopentadiene (DCPD) results in a concomitant polymerization exotherm of approximately 180° C. The internal temperature of the in situ generated polymer rises above the glass transition temperature (Tg=150° C.) of polyDCPD. Thus, in certain polymerization reactions, this polymerization exotherm and the temperature excursion provide for excellent monomer to polymer conversions. In this invention, it is preferable if the internal temperature of the polymer formulation should rise to about the deprotection temperature of the NHC—$X^2$—Y species.

In order to harness as much of the polymerization energy as possible, thereby driving the deprotection reaction to completion and, at the same time, the conversion of monomer to polymer, the polymerization enthalpy per unit mass of the monomer should preferably be high. It is desirable to achieve the release all the polymerization energy in ROMP or addition polymerization such that the internal temperature of the polymer reaches to about its glass transition temperature or beyond. In other words, the higher the double bond concentration in a unit mass of monomer the higher the potential polymerization exotherm energy. Therefore, it is desirable to have monomers that exhibit a low carbon to norbornene double bond ratio. For instance, the carbon atoms to double bond ratio in norbornene is 7. In heptylnorbornene the ratio is 14. Therefore, a mass of polymerizing norbornene would be expected to reach an internal temperature of approximately twice that of heptylnorbornene. For polycyclicolefin polymerization, the polymerization reaction time frame should preferably be short to ensure that the internal temperature of the polymer being formed can reach a high temperature.

Monomers possessing a low carbon to norbornene bond ratio are norbornene (ratio of 7), dimethanohexahydronaphthalene (TDD) (ratio of 6), and norbornadiene dimer (ratio of 7) are favored in this invention. In addition, the glass transition temperature of the final polymer is also important in selecting the starting monomer identities.

Monomers

The $NHC\text{—}X^2\text{—}Y$ derived initiator systems of the present invention are suitable for the preparation of a wide range of polymers comprising polymerized cyclic and linear repeating units. The cyclic olefin based polymers are prepared by the ring-opening metathesis polymerization or addition polymerization of a polycycloolefin monomer(s) in the presence of a catalytic amount of an initiator and NHC precursor mixture. The monomer(s) may be polymerized in the presence or absence of solvent.

Cyclic olefins are those simple olefins, such as cyclopropene, cyclobutene, cyclopentene, methylcyclopentene, cycloheptene, cyclooctene, 5-acetoxycyclooctene, 5-hydroxycyclooctene, cyclooctadiene, cyclotetraene, cyclcodecene, and cyclododecene.

As stated herein the terms "polycycloolefin," "polycyclic", and "norbornene-type" monomer are used interchangeably and mean that the monomer contains at least one norbornene moiety as shown below:

The simplest polycyclic monomer of the invention is the bicyclic monomer, bicyclo[2.2.1]hept-2-ene, commonly referred to as norbornene. The term norbornene-type monomer is meant to include norbornene, substituted norbornene(s), and any substituted and unsubstituted higher cyclic derivatives thereof so long as the monomer contains at least one norbornene or substituted norbornene moiety. The substituted norbornenes and higher cyclic derivatives thereof contain a pendant hydrocarbyl substituent(s) or a pendant functional substituent(s). The norbornene-type monomers are represented by the structure below:

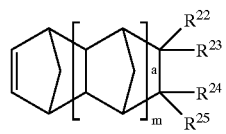

wherein "a" represents a single or double bond, $R^{22}$ to $R^{25}$ independently represents a hydrocarbyl or functional substituent, m is an integer from 0 to 5, and when "a" is a double bond one of $R^{22}$, $R^{23}$ and one of $R^{24}$, $R^{25}$ is not present.

When the substituent is a hydrocarbyl group, halohydrocarbyl, or perhalocarbyl group $R^{22}$ to $R^{25}$ independently represent hydrocarbyl, halogenated hydrocarbyl and perhalogenated hydrocarbyl groups selected from hydrogen, linear and branched $C_1$–$C_{10}$ alkyl, linear and branched, $C_2$–$C_{10}$ alkenyl, linear and branched $C_2$–$C_{10}$ alkynyl, $C_4$–$C_{12}$ cycloalkyl, $C_4$–$C_{12}$ cycloalkenyl, $C_6$–$C_{12}$ aryl, and $C_7$–$C_{24}$ aralkyl, $R^{22}$ and $R^{23}$ or $R^{24}$ and $R^{25}$ can be taken together to represent a $C_1$–$C_{10}$ alkylidenyl group. Representative alkyl groups include but are not limited to methyl, ethyl, propyl, isopropyl, butyl, isobutyl, sec-butyl, tert-butyl, pentyl, neopentyl, hexyl, heptyl, octyl, nonyl, and decyl. Representative alkenyl groups include but are not limited to vinyl, allyl, butenyl, and cyclohexenyl. Representative alkynyl groups include but are not limited to ethynyl, 1-propynyl, 2-propynyl, 1-butynyl, and 2-butynyl. Representative cycloalkyl groups include but are not limited to cyclopentyl, cyclohexyl, and cyclooctyl substituents. Representative aryl groups include but are not limited to phenyl, naphthyl, and anthracenyl. Representative aralkyl groups include but are not limited to benzyl, and phenethyl. Representative alkylidenyl groups include methylidenyl, and ethylidenyl, groups.

The preferred perhalohydrocarbyl groups include perhalogenated phenyl and alkyl groups. The halogenated alkyl groups useful in the invention are linear or branched and have the formula $C_zX'''_{2z+1}$ wherein $X'''$ can be selected from the same groups as X and $X^1$ as set forth above and z is selected from an integer of 1 to 10. Preferably $X'''$ is fluorine. Preferred perfluorinated substituents include perfluorophenyl, perfluoromethyl, perfluoroethyl, perfluoropropyl, perfluorobutyl, and perfluorohexyl. In addition to the halogen substituents, the cycloalkyl, aryl, and aralkyl groups of the invention can be further substituted with linear and branched $C_1$–$C_5$ alkyl and haloalkyl groups, aryl groups and cycloalkyl groups.

When the pendant group(s) is a functional substituent, $R^{22}$ to $R^{25}$ independently represent a radical selected from the group consisting of —$(CH_2)_nC(O)OR^{26}$, —$(CH_2)_n$—$C(O)OR^{26}$, —$(CH_2)_n$—$OR^{26}$, —$(CH_2)_n$—$OC(O)R^{26}$, —$(CH_2)_n$—$C(O)R^{26}$, —$(CH_2)_n$—$OC(O)OR^{26}$, —$(CH_2)_n SiR^{26}$, —$(CH_2)_n Si(OR^{26})_3$, and —$(CH_2)_n C(O)OR^{27}$, wherein n independently represents an integer from 0 to 10 and $R^{26}$ independently represents hydrogen, linear and branched $C_1$–$C_{10}$ alkyl, linear and branched, $C_2$–$C_{10}$ alkenyl, linear and branched $C_2$–$C_{10}$ alkynyl, $C_5$–$C_{12}$ cycloalkyl, $C_6$–$C_{14}$ aryl, and $C_7$–$C_{24}$ aralkyl. Representative hydrocarbyl groups set forth under the definition of $R^{26}$ are the same as those identified above under the definition of $R^{22}$ to $R^{25}$. As set forth above under $R^{22}$ to $R^{25}$, the hydrocarbyl groups defined under $R^{26}$ can be halogenated and perhalogenated. The $R^{27}$ radical represents a moiety selected from —$C(CH_3)_3$, —$Si(CH_3)_3$, —$CH(R^{28})OCH_2CH_3$, —$CH(R^{28})OC(CH_3)_3$ or the following cyclic groups:

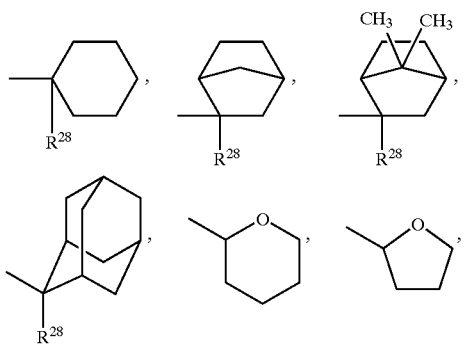

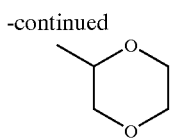

wherein $R^{28}$ represents hydrogen or a linear or branched ($C_1$–$C_5$) alkyl group. The alkyl groups include methyl, ethyl, propyl, i-propyl, butyl, i-butyl, t-butyl, pentyl, t-pentyl and neopentyl. In the above structures, the single bond line projecting from the cyclic groups indicates the position where the cyclic group is bonded to the acid substituent. Examples of $R^{27}$ radicals include 1-methyl-1-cyclohexyl, isobornyl, 2-methyl-2-isobornyl, 2-methyl-2-adamantyl, tetrahydrofuranyl, tetrahydropyranoyl, 3-oxocyclohexanonyl, mevalonic lactonyl, 1-ethoxyethyl, and 1-t-butoxy ethyl.

The $R^{27}$ radical can also represent dicyclopropylmethyl (Dcpm), and dimethylcyclopropylmethyl (Dmcp) groups, which are represented by the following structures:

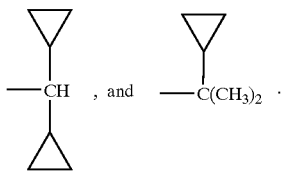

In the structure above, $R^{22}$ to $R^{25}$ together with the two ring carbon atoms to which they are attached can represent a substituted or unsubstituted cycloaliphatic group containing 4 to 30 ring carbon atoms or a substituted or unsubstituted aryl group containing 6 to 18 ring carbon atoms or combinations thereof. The cycloaliphatic group can be monocyclic or polycyclic. When unsaturated the cyclic group can contain monounsaturation or multiunsaturation, with monounsaturated cyclic groups being preferred. When substituted, the rings contain monosubstitution or multisubstitution wherein the substituents are independently selected from hydrogen, linear and branched $C_1$–$C_5$ alkyl, linear and branched $C_1$–$C_5$ haloalkyl, linear and branched $C_1$–$C_5$ alkoxy, halogen, or combinations thereof. $R^{22}$ to $R^{25}$ can be taken together to form the divalent bridging group, —C(O)—Q—(O)C—, which when taken together with the two ring carbon atoms to which they are attached form a pentacyclic ring, wherein Q represents an oxygen atom or the group N($R^{29}$), and $R^{29}$ is selected from hydrogen, halogen, linear and branched $C_1$–$C_{10}$ alkyl, and $C_6$–$C_{18}$ aryl. A representative structure is shown in below:

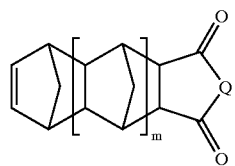

wherein m is an integer from 0 to 5.

Crosslinked polymers can be prepared by copolymerizing the norbornene-type monomer(s) set forth under Structure VII above with a multifunctional norbornene-type crosslinking monomer(s). By multifunctional norbornene-type crosslinking monomer is meant that the crosslinking monomer contains at least two norbornene-type moieties, each functionality being addition, ROMP, CM, ADMET, RCM, and OM polymerizable in the presence of the catalyst system of the present invention. In the case of CM, ADMET and RCM reactions, the functionality comprises one or more acyclic olefins. The crosslinkable monomers include fused multicyclic ring systems and linked multicyclic ring systems. Examples of fused crosslinkers are illustrated in structures below. For brevity, norbornadiene is included as a fused multicyclic crosslinker.

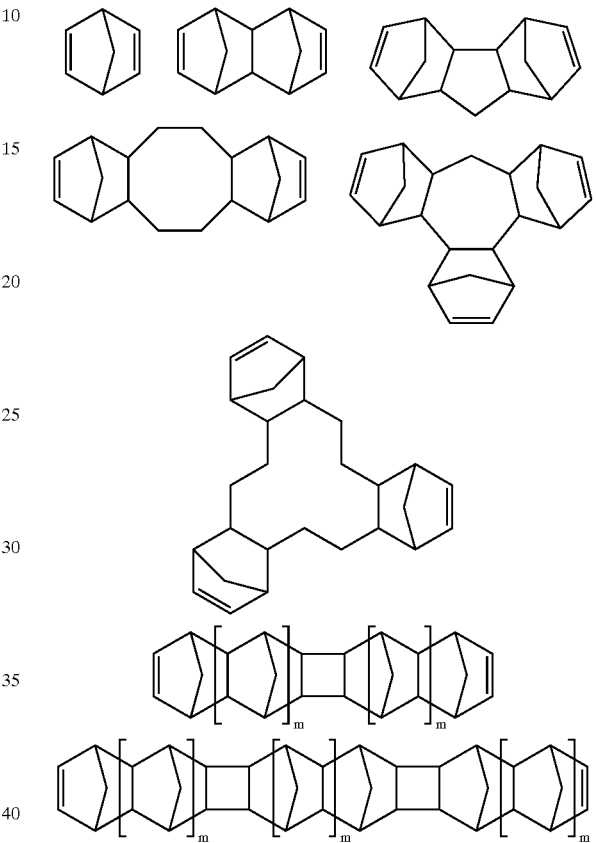

wherein m independently is an integer from 0 to 5.

A linked multicyclic crosslinker is illustrated generically in structure below.

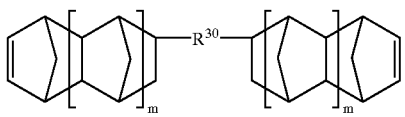

wherein m independently is an integer from 0 to 5, $R^{30}$ is a divalent radical selected from divalent hydrocarbyl and silyl radicals and divalent ether radicals. By divalent is meant that a free valence at each terminal end of the radical is attached to a norbornene-type moiety.

Preferred divalent hydrocarbyl radicals are alkylene radicals and divalent aromatic radicals. The alkylene radicals are represented by the formula —($C_dH_{2d}$)— where d represents the number of carbon atoms in the alkylene chain and is an integer from 1 to 10. The alkylene radicals are preferably selected from linear and branched ($C_1$–$C_{10}$) alkylene such as methylene, ethylene, propylene, butylene, pentylene, hexylene, heptylene, octylene, nonylene, and decylene. When branched alkylene radicals are contemplated, it is to be understood that a hydrogen atom in the alkylene backbone is replaced with a linear or branched ($C_1$ to $C_5$) alkyl group. Preferred silyl radical can be selected from $CH_2OSi(R)_2OCH_2$, where R=methyl, ethyl, butyl, allyl, propyl, benzyl, or phenyl.

The divalent aromatic radicals are selected from divalent phenyl, and divalent naphthyl radicals. The divalent ether radicals are represented by the group —$R^{31}$—O—$R^{31}$—, wherein $R^{31}$ independently is the same as $R^{30}$. Examples of specific linked multicyclic crosslinkers are represented as in Structures VIIIa to VIIIc as follows.

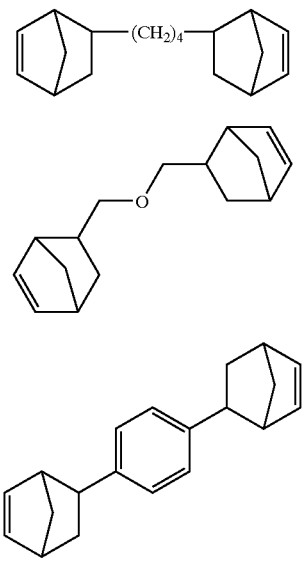

Examples of preferred di and polyfunctional crosslinkable monomers include:

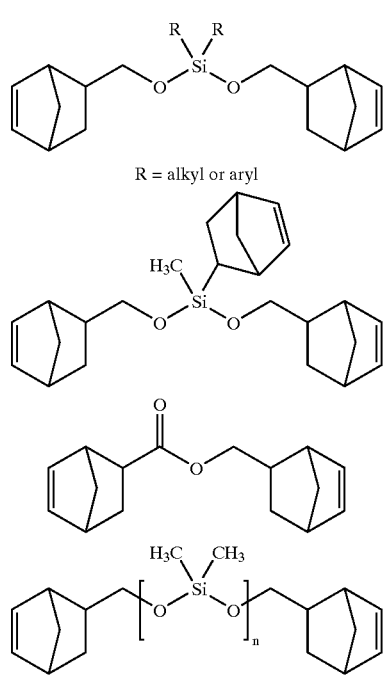

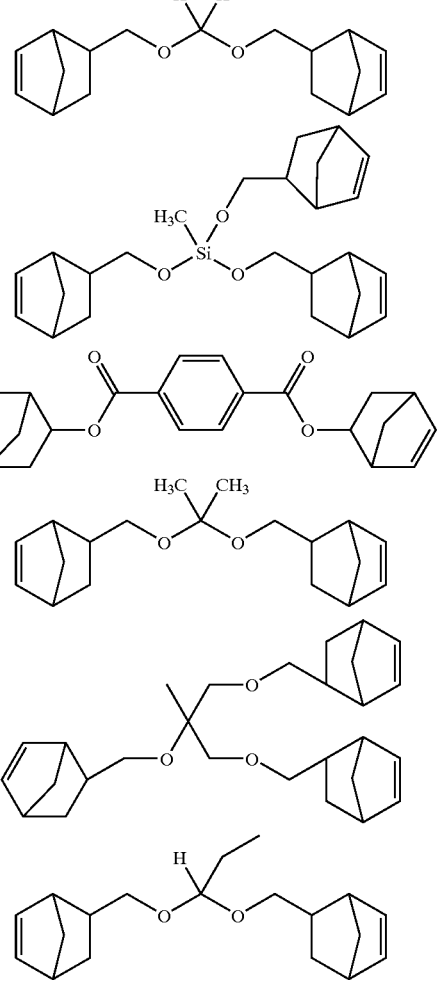

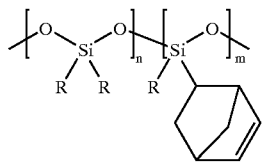

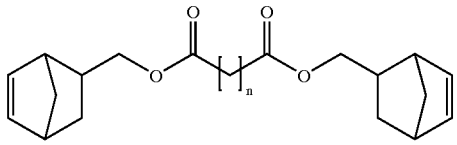

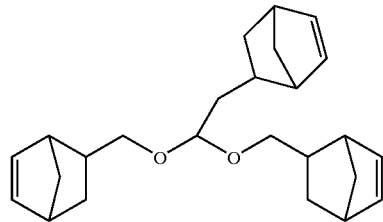

One economical route for the preparation of hydrocarbyl substituted and functionally substituted norbornene monomers employs the Diels-Alder addition reaction in which CPD or substituted CPD is reacted with a suitable dienophile at elevated temperatures to form the substituted norbornene-type adduct generally shown by the following reaction scheme 23:

SCHEME 23

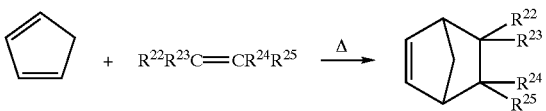

wherein $R^{22}$ to $R^{25}$ independently represent hydrogen, hydrocarbyl, and/or a functional group as previously described.

Other norbornene type adducts can be prepared by the thermal pyrolysis of dicyclopentadiene (DCPD) in the presence of a suitable dienophile. The reaction proceeds by the initial pyrolysis of DCPD to CPD followed by the Diels-Alder addition of CPD and the dienophile to give the adducts shown below in Scheme 24:

SCHEME 24

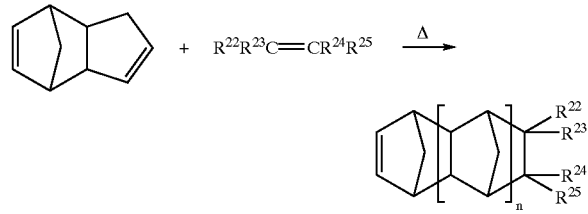

wherein n represents the number of cyclic units in the monomer and $R^{22}$ to $R^{25}$ independently represent hydrogen, hydrocarbyl, and/or a functional group as previously defined. Norbornadiene and higher Diels-Alder adducts thereof similarly can be prepared by the thermal reaction of CPD and DCPD in the presence of an acetylenic reactant as shown below in Scheme 25:

SCHEME 25

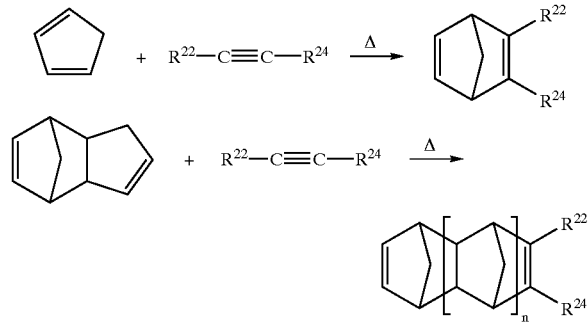

wherein n, $R^{22}$ and $R^{24}$ are as defined above.

Norbornadiene may be employed as a crosslinker in this invention, however, higher homologs are preferred. Norbornadiene can be converted into higher homologs or Diels-Alder products using a variety of dimerization catalysts or heating it with cyclopentadiene. In the case of the crosslinking monomer norbornadiene dimer an alternative synthesis is employed in which norbornadiene is coupled catalytically to yield a mixture of isomers of norbornadiene dimer as shown below:

SCHEME 26

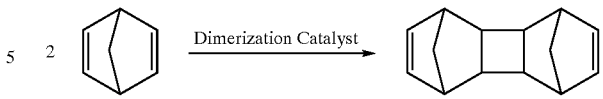

The dimerization of norbornadiene is easily achieved by numerous catalysts to yield a mixed composition of up to six isomers, as described in, for example, U.S. Pat. No. 5,545,790, the contents of which are incorporated herein by reference. The preferred isomers are the exo-trans-exo, endo-trans-endo, and exo-trans-endo-1,4,4a,4b,5,8,8a,8b-octahydro-1,4:5,8-dimethanobiphenylene ("norbornadiene dimer" or "[NBD]$_2$"). The exo-trans-exo norbornadiene dimer is the most preferred crosslinker. Heating norbornadiene dimer with dicyclopentadiene or cyclopentadiene can produce higher oligomers of norbornadiene dimer. Other crosslinkers are prepared by the reaction of cyclopentadiene with olefins containing two or more reactive olefins, e.g., cyclooctadiene, 1,5-hexadiene, 1,7-octadiene, and tricycloheptatriene.

The more preferred crosslinkable monomers are those containing two reactive norbornene type moieties. One preferred monomer is 5,5'-(1,2-ethanediyl)bisbicyclo[2.2.1]hept-2-ene (NBCH$_2$CH$_2$NB) prepared by the reaction of 5-(3-butenyl)bicyclo[2.2.1]hept-2-ene and cyclopentadiene via a Diels-Alder reaction. The higher homolog of 5-(3-butenyl)bicyclo[2.2.1]hept-2-ene is also a co-monomer of choice, i.e., 2-(3-butenyl)-1,2,3,4,4a,5,8,8a-octahydro-1,4:5,8-dimethanonaphthalene. Similarly, 1, 4, 4a, 5, 6, 6a, 7, 10, 10a, 11, 12, 12a-dodecahydro-1,4:7,10-dimethanodibenzo[a,e]cyclooctene is prepared in the Diels Alder reaction between 1, 4, 4a, 5, 6, 9, 10, 10a-octahydro-1,4-methanobenzocyclooctene and cyclopentadiene. The higher homolog of between 1, 4, 4a, 5, 6, 9, 10, 10a-octahydro-1,4-methanobenzocyclooctene is also a comonomer of choice, i.e., 1,4,4a,5,5a,6,7,10,11,11a,12,12a-dodecahydro-1,4:5,12-dimethanocycloocta[b]naphthalene. The symmetric and asymmetric trimers of cyclopentadiene are also useful crosslinking reagents, i.e., 4, 4a, 4b, 5, 8, 8a, 9, 9a-octahydro-1,4:5,8-dimethano-1H-fluorene and 3a,4,4a, 5, 8, 8a, 9, 9a-octahydro-4,9:5,8-dimethano-1H-benz[f]indene. Another preferred monomer is obtained from the reaction of cyclopentadiene and norbornadiene, i.e., 1,4,4a,5,8,8a-hexahydro-1,4:5,8-dimethanonaphthalene. Divinylbenzene and excess cyclopentadiene forms the symmetric crosslinker 5,5'-(1,4-phenylene)bisbicyclo[2.2.1]hept-2-ene.

Examples of preferred polymerizable norbornene-type monomers include but are not limited to, norbornene (bicyclo[2.2.1]hept-2-ene), 5-methyl-2-norbornene, ethylnorbornene, propylnorbornene, isopropylnorbornene, butylnorbornene, isobutylnorbornene, pentylnorbornene, hexylnorbornene, heptylnorbornene, octylnorbornene, decylnorbornene, dodecylnorbornene, octadecylnorbornene, p-tolylnorbornene, methylidene norbornene, phenylnorbornene, ethylidenenorbornene, vinylnorbornene, exo-dicyclopentadiene, endo-dicyclopentadiene, tetracyclododecene, methyltetracyclododecene, tetracyclododecadiene, dimethyltetracyclododecene, ethyltetracyclododecene, ethylidenyl tetracyclododecene, phenyltetracyclodecene, symmetrical and unsymmetrical trimers and tetramers of cyclopentadiene, 5,6-dimethylnorbornene, propenylnorbornene, 5,8-methylene-5a,8a-dihydrofluorene, cyclohexenylnorbornene, dimethanohexahydronaphthalene, endo,exo-5,6- dimethoxynorbornene, endo,endo-5,6-dimethoxynorbornene, 2,3-dimethoxynorbornadiene, 5,6-bis(chloromethyl)bicyclo[2.2.1]hept-2-ene, 5-tris(ethoxy)silylnorbornene, 2-dimethylsilylbicyclo[2.2.1]hepta-2,5-diene, 2,3-bistrifluoromethylbicyclo[2.2.1]hepta-2,5-diene, 5-fluoro-5-pentafluoroethyl-6-,6-bis(trifluoromethyl)bicyclo[2.2.1]hept-2-ene, 5,6-difluoro-5-heptatafluoroisopropyl-6-trifluoromethyl)bicyclo[2.2.1]hept-2-ene, 2,3,3,4,4,5,5,6-octafluorotricyclo[5.2.1.O]dec-8-ene, and 5-trifluoromethylbicyclo[2.2.1]hept-2-ene, 5,6-dimethyl-2-norbornene, 5-a-naphthyl-2-norbornene, 5,5-dimethyl-2-norbornene, 1,4,4a,9,9a,10-hexahydro-9,10[1',2']-benzeno-1,4-methanoanthracene, indanylnorbornene (i.e., 1,4,4,9-tetrahydro-1,4-methanofluorene, the reaction product of CPD and indene), 6,7,10,10-tetrahydro-7,10-methanofluoranthene (i.e., the reaction product of CPD with acenaphthalene), 1,4,4,9,9,10-hexahydro-9,10[1',2']-benzeno-1,4-methanoanthracene, endo,endo-5,6-dimethyl-2-norbornene, endo,exo-5,6-dimethyl-2-norbornene, exo,exo-5,6-dimethyl-2-norbornene, 1,4,4,5,6,9,10,13,14,14-decahydro-1,4-methanobenzocyclododecene (i.e., reaction product of CPD and 1,5,9-cyclododecatriene), 2,3,3,4,7,7-hexahydro-4,7-methano-1H-indene (i.e., reaction product of CPD and cyclopentene), 1,4,4,5,6,7,8,8-octahydro-1,4-methanonaphthalene (i.e., reaction product of CPD and cyclohexene), 1,4,4,5,6,7,8,9,10,10-decahydro-1,4-methanobenzocyclooctene (i.e., reaction product of CPD and cyclooctene), and 1,2,3,3,3,4,7,7,8,8,decahydro-4,7-methanocyclopent[a]indene.

Particularly useful monomers are those that contain more than one polymerizable double bonds because they are capable of releasing more energy but also because they can link polymer chains. The smallest polycyclic structure is norbornadiene which has a carbon to polymerizable double bond ratio of 3.5, i.e., two double bonds per 7-carbons. Polycyclic structures useful in the polymerizations can be derived from norbornadiene and its products. These monomers are dimeric and trimeric crosslinking agents, and isomerized products of norbornadiene, i.e.,

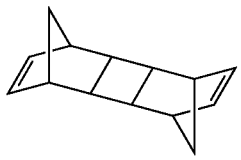

Norbornadiene Dimer
exo-trans-exo (2+2 dimer)

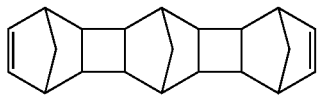

Norbornadine Trimer

Norbornadiene Dimer
exo-trans (4+2 dimer)

-continued

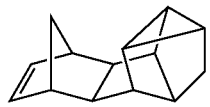

Norbornadiene Dimer
exo-ciss (4+2 dimer)

The cycloolefin monomers contemplated herein also include monomers disclosed in U.S. Pat. Nos. 4,301,306 and 4,324,717, the contents of each of which are incorporated herein by reference. Both of these references disclose monomers that contain the norbornene structure depicted above.

The invention may also be used with to polymerize "norbornene-type monomers" which include norbornene, dicyclopentadiene, tricyclopentadiene (symmetrical and unsymmetrical cyclopentadiene trimer), tetracyclododecene and other cycloolefin monomers containing a norbornene functional group. Dicyclopentadiene is a common cycloolefin monomer used to prepare ring-opened metathesis polymerized polymers in that it is readily available as a by-product in ethylene production. For such polymerizations, liquid reagents are preferred in that they are handled more easily than solids, provided they are not too viscous. Problems may arise with the use of dicyclopentadiene in that it is a solid at ambient temperature when sufficiently pure. The melting point for high purity dicyclopentadiene is generally above about 31° C. to 32° C. Although dicyclopentadiene can be rendered liquid with slight heating, this high melting temperature may present a significant disadvantage commercially. In addition, when shipping the monomer, considerable trouble and expense may be realized in melting the monomers when they arrive at their destination. High purity dicyclopentadiene is preferable for polymerization; however, high purity is not required. Nonetheless, impurities will often provide liquid dicyclopentadiene mixtures but may also retard polymerization. Adding an inert solvent or diluent may adversely affect the products obtained in that the unreacted component may reduce impact properties and/or leach from the finished polymer, rendering it useless.

Likewise, it should be noted that the utility of norbornene monomer (bicyclo[2.2.1]hept-2-ene) in certain applications may be reduced because it is also a solid at room temperature. In addition, norbornene is characterized by its relatively low boiling point and flash point. The preferred norbornene-type monomers are mixtures of endo-and exo-stereoisomers, since these materials are often liquids. The use of two or more different monomers is preferred. Mixing components depresses the freezing points of the monomer mix in contrast with using a single monomer component. In this way the monomer mixture is usable under a wider range of handling conditions. When a solid norbornene-type monomer is employed, the monomer can be dissolved or swollen in solvent or co-mixed with other monomers. Also, a solid norbornene-type monomer(s) can be efficiently polymerized by heating the monomer(s) to its melting point, or beyond, and inducing dissolution of the ingredients of the catalyst system.

Norbornene-type monomers prepared by the Diels-Alder reaction are obtained as endo or exo isomers in varying compositions dependant on the starting dienophiles. The endo and exo forms of the norbornene-type monomers are essentially incorporated equally into the polymer. If, however, for a particular reason one isomer composition is favored over another, e.g., monomer composition is liquid at room temperature, then the reaction monomers may be isomerized in the presence of a suitable Lewis acid or solid acid. The endo-form of aromatic group-containing norbornene-type monomers can be converted to their exo-form yielding an isomer mixture of aromatic group-containing norbornene-type monomers by contacting a solid acid catalyst with endo-isomers to obtain an exo-isomer-rich monomer mixture.

Monomer Purity

Commercial polycyclic olefins are available in various levels of purity, ranging from about 20% to about 99.9%, the upper purity ranges being the result of distillation, cracking and reforming, and further treatment for removal of contamination and olefins which would not co-polymerize under polymerization conditions. Purity further reflects the overall composition of the monomer, excluding any trimers or tetramers or any higher oligomers.

The polycyclic monomers used in this invention may contain a nominal amount of similar hydrocarbons, however, if present should not be of a type which could adversely affect the reaction. If the norbornene-type monomer employed contains undesirable hydrocarbons, the later can be removed by known means. It is preferred to remove any impurities that may interfere with the polymerization reaction. Even after these steps have been taken the monomer may still contain some impurities. The purity of the monomers should preferably be greater than about 90%, more preferably greater than about 95% pure, and still more preferably greater than about 99%, and most preferably above about 99.5% to ensure as complete as possible monomer to polymer conversion.

Water and oxygenated products, inadvertently added to the formulation components during their preparation, may be detrimental to the storage stability of the initiator components. Water can enter the formulation as an impurity in the cycloolefin monomers and in the inert compounding ingredients that are mainly impact modifiers, plasticizers, flame retardants, blowing agents, fillers and reinforcements. Before either the NHC—$X^2$—Y or initiator is added to the formulation, the level of water in the mixture of cycloolefin monomers and inert compounding ingredients preferably should be lower than approximately 50 ppm, and more preferably between about 10 and 0 ppm. To be assured that the level of water in the cycloolefin monomers is less than 10 ppm before the NHC-precursor or initiator is added, it can be dried via azeotropic distillation. Because water and most cycloolefin monomers form heterogeneous azeotropes, distilling off a small portion of the cycloolefin monomers will remove most of the water contamination. Traditionally, residual water can be removed by adding molecular sieves to the cyclic olefins.

Polymerization

Broadly stated, the process of the invention involves forming a reactive monomer composition such that the propagating species is formed in situ. The reaction can occur in the presence or absence of a solvent for the metal carbene metathesis catalyst or the NHC precursor or the norbornene-type monomer to be polymerized. In one embodiment of the invention an alkylidene is combined with the NHC precursor component and a norbornene-type monomer. In another embodiment an alkylidene is combined with a NHC precursor and a moderating component and a norbornene-type monomer. In an alternative embodiment a solution of the thermally treated NHC precursor and initiator is combined with at least one norbornene-type monomer. In this embodiment suitable solvents for the catalyst component include but are not limited to alkane and cycloalkane solvents such as pentane, hexane, heptane, and cyclohexane; halogenated alkane solvents such as dichloromethane, chloroform, carbon tetrachloride, ethylchloride, 1,1-dichloroethane, 1,2-dichloroethane, 1-chloropropane, 2-chloropropane, 1-chlorobutane, 2-chlorobutane, 1-chloro-2-methylpropane, and 1-chloropentane; ethers such as THF and diethylether; aromatic solvents such as benzene, xylene, toluene, mesitylene, chlorobenzene, and o-dichlorobenzene; and halocarbon solvents such as Freon® 112; and mixtures thereof. Preferred solvents include benzene, fluorobenzene, o-difluorobenzene, p-difluorobenzene, pentafluorobenzene, hexafluorobenzene, o-dichlorobenzene, chlorobenzene, toluene, o-, m-, and p-xylenes, mesitylene, cyclohexane, THF, dichloromethane, liquid rubbers, and liquid antioxidants.

Monomer to Initiator Reactant Ratio

Preferably the monomer to initiator (based on Ru or Os) molar ratio from about 100:1 to about 1,000,000:1, more preferably from about 100:1 to about 500,000:1. Even more preferably the monomer to initiator molar ratio is from about 1000:1 to about 100,000:1, and most preferably from about 5,000:1 to about 60,000:1.

NHC—$X^2$—Y to Initiator Reactant Ratio

Preferably the NHC—$X^2$—Y to initiator (based on Ru or Os) molar ratio preferably from about 25:1 to about 0.1:1 on a molar basis, more preferably about 5:1 to about 0.5:1, and most preferably about 2:1 to about 1:1.

Monomer Temperature

The rate of polymerization will depend on the initiation temperature, therefore gel and cure times can be controlled by adjusting the polymerization temperature. In general, as the temperature at which the reaction is carried out is increased the reaction rate will also increase. For every 8° C. temperature rise the reaction rate will approximately double. Consequently, to keep the reaction rate controlled at higher reaction temperatures a less active formulation of the polymerization catalyst system may be used. As the temperature at which the reaction is carried out is increased, the gel and cure times will decrease.

After the polymerization reaction is complete, the polymer may be subjected to an additional post cure treatment at a temperature in the range of about 100° C. to 300° C. for about 15 minutes to 24 hours, preferable 1 to 2 hours. Such a post cure treatment can enhance polymeric properties including glass transition temperature and heat distortion temperature. In addition, postcuring is desirable but not essential, to bring the samples to their final stable dimensional states, to minimize residual odors, and to improve final physical properties. The invention process may be used to prepare either a norbornene type thermoplastic homopolymer or copolymer or a thermosetted norbornene type homopolymer or copolymer.

Polymerization Time

Once the polymerization is initiated, polymerization should occur quite rapidly, usually within approximately one minute and preferable within approximately 10 seconds, and is accompanied by a rapid rise in temperature. The time required to complete polymerization, however, is a function of the reactivity of the monomer and the initiator, rate of deprotection of the NHC—$X^2$—Y. Substantially complete reactions may be obtained in as little at one second or over a period as long as several hours. One advantage of NHC—$X^2$—Y polymerization thermoset recipes is that they do not gel up as rapidly as previous ROMP formulations.

Modifying Rate of Catalyst Generation, Controlling Catalyst Reactivity, and Polymerization Activity The present invention may be practiced under a relatively wide variety of conditions of reaction time, temperature, pressure, reactant phase, and mixing. Selection of conditions is a function of the activity and selectivity of the initiator, rate of deprotection of the NHC—$X^2$—Y and the type of polymer desired.

Control over gel and cure time is particularly important in polymerization reactions. The control of gel and cure in this invention is derived from a number of sources. "Indigenous" (meaning native or established by the components) or "exogeneous" (meaning external additives or other reactives that can be added to the system).

By far the simplest method of controlling the reactivity of the catalyst system is to regulate the character of the ligands attached to the ruthenium or osmium derivatives. Correct ligand selection is important with regard to the indigenous reactivity control agents. For example, $RuCl_2(PPh_3)_2$ (=CHPh) reacts more slowly than the $RuCl_2(PCy_3)_2$ (=CHPh). The catalyst substituents may also be changed to control the gel and cure times of the of the generated catalyst system. Likewise, the character of the leaving group ($X^2$—Y) of the NHC—$X^2$—Y can influence the rate of the reaction, i.e., $CHCl_3$. eliminates more cleanly from the NHC—$X^2$—Y than does $HOCMe_3$. Similarly, the desired gel and cure of the system can be achieved by proper selection of a rate moderating ligand (exogenous reactivity control).

The use of Lewis base rate moderators in this system is optional, i.e., external or "exogeneous" modification, resulting in further gel and cure time control. Suitable exogeneous rate moderators include, for example, water, tetrahydrofuran (THF), 2-methyltetrahydrofuran (2-Me—THF), diethyl ether (($C_2H_5)_2O$), methyl-tert-butyl ether ($CH_3OC(CH_3)_3$), dimethoxyethane ($CH_3OCH_2CH_2OCH_3$), diglyme ($CH_3OCH_2OCH_2OCH_3$), trimethylphosphine ($PMe_3$), triethylphosphine ($PEt_3$), tributylphosphine ($PBu_3$), tri(ortho-tolyl)phosphine (P-o-tolyl$_3$), tri-tert-butylphosphine (P-tert-Bu$_3$), tricyclopentylphosphine ($PCp_3$), tricyclohexylphosphine ($PCy_3$), triisopropylphosphine (P-i-Pr$_3$), trioctylphosphine ($POct_3$), triphenylphosphine ($PPh_3$), tri(pentafluorophenyl)phosphine ($P(C_6F_5)_3$), methyldiphenylphosphine ($PMePh_2$), dimethylphenylphosphine ($PMe_2Ph$), trimethylphosphite ($P(OMe)_3$), triethylphosphite ($P(OEt)_3$), triisopropylphosphite ($P(O-i-Pr)_3$), ethyl diphenylphosphinite ($P(OEt)Ph_2$), tributylphosphite ($P(OBu)_3$), triphenylphosphite ($P(OPh)_3$), diethylphenylphosphonite ($P(OEt)_2Ph$), and tribenzylphosphine ($P(CH_2Ph)_3$), 2-cyclohexenone, and triphenylphosphine oxide. The preferred exogeneous rate moderators are triphenylphosphine and triphenylphosphine oxide.

Further, the exogeneous control over reactivity can be achieved by attaching the Lewis base species to a polymerizable monomer. In this way, the moderator can be polymerized into the polymeric structure giving the system important functionality. Examples of suitable functional groups are ethers, trialkoxysilanes, esters, carboxylic acids, and alcohols. Specific examples are triethoxysilylnorbornene, norbornene methanol, and butoxynorbornene.

Other Components

Various additives can be included to modify the properties of polycyclic olefin polymers. The polymerization can be carried out in the presence of non-interfering additives, such as, for example, solvents, blowing agents, fillers, fibers, pigments, dyes, lubricants, antioxidants, antiozonants, UV absorbing agents, crosslinking agents, odor absorbing or masking agent, flame retardants, light stabilizers, plasticizers, foaming agents, whiskers for surface smoothing, tougheners, reinforcing agents, organic liquids, inorganic liquids, UV stabilizing agents, electromagnetic radiation absorbing materials, electromagnetic radiation reflecting materials, electromagnetic radiation emitting materials, electromagnetic radiation conducting materials, physical bonding agents, mechanical bonding agents, chemical bonding agents, thermal or electrical conducting materials or agents, thermal or electrical insulating materials, radioactive absorbing materials, radioactive emitting materials, radioactive reflecting materials, radioactive absorbing materials, radioactive conducting materials, sacrificial materials or additives for corrosive applications or environments, nano-sized fillers or reinforcements, impact and polymeric modifiers and viscosifiers. It is preferable that the additives not affect catalytic activity.

Antioxidants and antiozonants include any antioxidant or antiozonant used in the rubber or plastics industry. An "Index of Commercial Antioxidants and Antiozonants, Fourth Edition" is available from Goodyear Chemicals, The Goodyear Tire and Rubber Company, Akron, Ohio 44316. The antioxidants can be phenol, phosphorus, sulfur, or amine based compounds. The antioxidants can be used singly, or preferably, in combination. The formulation ratio is more than 0.05 part preferably 0.5 to 100 parts by weight of norbornene polymer. The antioxidant may be copolymerized with the monomer such as 5-(3,5-di-tert-butyl-4-hydroxybenzyl-2-norbornene, which is a norbornenylphenol based compound (See Japanese Kokai No: 57-83522)

The polymerization reaction may further contain stabilizers against oxidative degradation. Compounds selected for this purpose preferably should not interfere to a significant extent with the polymerization reaction. Suitable stabilizers may be selected from the following group: 2,6-di-tert-butyl-4-methylphenol (BHT); styrenated phenol, such as Wingstay S (Goodyear); 2- and 3-tert-butyl-4-methoxyphenol; alkylated hindered phenols, such as Wingstay C (Goodyear); 4-hydroxymethyl-2,6-di-tert-butylphenol; 2,6-di-tert-butyl-4-sec-butylphenol; 2,2'-methylenebis(4-methyl-6-tert-butylphenol); 2,2'-methylenebis(4-ethyl-6-tert-butylphenol); 4,4'-methylenebis(2,6-di-tert-butylphenol); miscellaneous bisphenols, such as Cyanox 53 and Permanax WSO; 2,2'-ethylidenebis(4,6-di-tert-butylphenol); 2,2'-methylenebis(4-methyl-6-(1-methylcyclohexyl)phenol); 4,4'-butylidenebis(6-tert-butyl-3-methylphenol); polybutylated Bisphenol A; 4,4'-thiobis(6-tert-butyl-3-methylphenol); 4,4'-methylenebis(2,6-dimethylphenol); 1,1'-thiobis(2-naphthol); methylene bridged polyaklylphenol, such as Ethyl antioxidant 738; 2,2'-thiobis (4-methyl-6-tert-butylphenol); 2,2'-isobutylidenebis(4,6-dimethylphenol); 2,2'-methylenebis(4-methyl-6-cyclohexylphenol); butylated reaction product of p-cresol and dicyclopentadiene, such as Wingstay L; tetrakis (methylene-3,5-di-tert-butyl-4-hydroxyhydrocinnamate) methane, i.e., Irganox 1010; 1,3,5-trimethyl-2,4,6-tris(3,5-di-tert-butyl-4-hydroxybenzyl)benzene, e.g., Ethanox 330; 1,3,5-tris(3,5-di-tert-butyl-4-hydroxybenzyl)isocyanurate, i.e., Good-rite 3114, 2,5-di-tert-amylhydroquinone, tert-butylhydroquinone, tris(nonylphenylphosphite), bis(2,4-di-tert-butyl)pentaerythritol)diphosphite, distearyl pentaerythritol diphosphite, phosphited phenols and bisphenols, such as Naugard 492, phosphite/phenolic antioxidant blends, such as Irganox B215; di-n-octadecyl(3,5-di-tert-butyl-4-hydroxybenzyl)phosphonate, such as Irganox 1093; 1,6-hexamethylene bis(3-(3,5-di-tert-butyl-4-hydroxyphenylpropionate), such as Irganox 259, and octadecyl-3,5-di-tert-butyl-4-hydroxyhydrocinnamate, i.e., Irganox 1076, tetrakis(2,4-di-tert-butylphenyl)4,4'-biphenylylenediphosphonite, diphenylamine, and 4,4'- diemthoxydiphenylamine. Such materials are normally employed at levels of about 0.05% to 5% based on the polymer, but more preferably 0.1% to 1% based on the polymer.

The method of this invention is also suitable for production of reinforced polymers by use of conventional fillers or reinforcing components or nano-sized fillers or reinforcing components, which may be in the form of particles, filaments, powders, fibers, tubes, granules, strands, beads, or other uniform or nonuniform geometric shapes. Examples of reinforcing components and/or fillers include segments of fiberglass or chopped fiberglass, fiberglass cloth or woven roving, fiberglass mat, carbon or graphite fibers, organic fibers, aramid fibers, inorganic fibers, wood pulp, wood flour, ground or pulverized oyster shells, metals, aluminum powder or flakes, calcium carbonate, thermoplastic or elastomer reinforcements or fillers, ground or pulverized thermoset polymers, silica, alumina, carbon black, silicates, aluminosilicates such as mica, talc, clays, sand, diatomaceous earth, volcanic glass, or ash, Nanostructured™ Chemicals such as polyhedral oligomeric silsesquioxane (POSS™) based materials, vermiculite, asbestos, and calcium silicates, such as wollastonite. These compounds increase the polymer's flexural modulus with only a small sacrifice in impact resistance. It is surprising that in spite of the highly polar nature of their surfaces these fillers can be added without appreciably affecting the polymerization rate. Preferably, such fillers may be surface treated with a silane coupling agent. From about 5% to about 75% by weight may be incorporated. This and all subsequent percentages are based on the weight of the final polymer. The addition of fillers that have modified surface properties are particularly advantageous. The exact amount of a particular filler to be used in a particular situation will be easily determinable and will depend on the preferences of the practitioner. After a short post cure at 150–200° C. an unfilled polymer will shrink from about 3.0 to about 3.5% whereas adding 20–25 wt % filler will decrease the shrinkage to 1.5–2% and adding 33 wt % filler will further decrease shrinkage to about 1%.

In some embodiments of this invention, a preformed elastomer may be added to the initiator system in order to increase the impact strength of the polymer or other mechanical properties. An important factor in selecting an elastomer is in its ability to dissolve in the monomer. A short dissolution time is preferred indicating that the elastomer is quite easily dissolved in the monomer. The addition of an elastomer can increase the polymer's impact strength 5–10 fold with only a slight decrease in flexural modulus. The elastomer is dissolved in the monomer in an amount from about 1 to about 15 weight percent, based on the weight of monomer. A preferred concentration range for the elastomer is between about 3 and about 10 wt %. The elastomer can be dissolved in the monomer in the 5–10 wt % range without causing an excessive increase in the solution viscosity. A target viscosity range at room temperature would about 100 to about 1000 cps and more preferable from about 200 to about 500 cps. It is preferable that the elastomer be miscible with the polycyclic olefin monomer between about 10° C. and about 100° C. Suitable elastomers include, for example, natural rubber, butyl rubber, polyisoprene, polybutadiene, polyisobutylene, ethylene-propylene copolymer, styrene-butadiene-styrene triblock rubber, random styrene-butadiene rubber, styrene-isoprene-styrene triblock rubber, ethylene-propylene-diene terpolymers, ethylene-vinyl acetate and nitrile rubbers. Preferred elastomers are polybutadiene Diene 55AC10 (Firestone), polybutadiene Diene 55AM5 (Firestone), EPDM Royalene 301T, EPDM Buna T9650 (Bayer), Polysar Butyl 301 (Bayer), polybutadiene Taktene 710 (Bayer), Ethylene-Octene Engage 8150 (DuPont-Dow), styrene-butadiene Kraton D1184 (Shell), EPDM Nordel 1070 (DuPont-Dow), and polyisobutylene Vistanex MML-140 (Exxon). Various polar elastomers can also be used. The amount of elastomer used is determined by its molecular weight. The Brookfield viscosity of polycyclic olefins are between about 5 to about 10 cps at 35° C. Increasing the viscosity to between about 100 cps to about 1000 cps is preferable in the polymerization reaction. An increase in viscosity simplifies the use of fillers by decreasing the settling rates of the solids.

As an alternative, preformed elastomers or polymers that are essentially insoluble in the monomer can also be used to improve impact resistance of ROMP and addition-polymerized norbornene monomers. Core shell polymer particles can be defined as polymer particles have a core and a shell having different physical and/or chemical properties. With elastomeric core-shell particles it is meant that at least the core of the particles consists of elastomeric material. Elastomeric core-shell polymer particles have found use in stabilizing the impact properties of some thermoset polymers of cycloolefins, such as ROMP DCPD polymers, as disclosed in PCT Publication No. WO 94/19385, the disclosure of which is incorporated herein by reference. Elastomeric core-shell particles of a size not exceeding about 2 $\mu$m are dispersed in the starting monomers in an amount of from about 0.5 to about 20 weight percent relative to the weight of the monomer. Elastomeric core-shell particle having a size in the range of from about 0.01 to about 2 $\mu$m and more preferably in the range of from about 0.1 to about 1 $\mu$m. Examples of elastomeric core-shell particles suitable for use in the present invention are those marketed under their trademark PARALOID EXL, and in particular the PARALOID EXL2300/3300 elastomeric core-shell polymer series and/or the PARALOID EXL2600/3600 elastomeric core-shell polymer series and/or the PARALOID KM elastomeric core-shell polymer series and/or the PARALOID BTA elastomeric core-shell polymer series.

Since sensitivity to added compounds may be different for each system, it is desirable to determine experimentally whether a compound to be added may interfere with the reaction.

EXAMPLES

The following examples are given for the purpose of illustration only and the invention is not to be regarded as limited to any of the specific materials or conditions used in the examples.

Commercially available or prepared polycyclic monomers used should preferably be of the highest purity. Typically monomers should be purified so that the polycyclic monomers contain no impurities that reduce catalyst activity. This may be achieved by distillation or by passing the monomers through a BTS and a 3A molecular column for removal of residual oxygen and water, respectively, before use. It is often desirable to purify the starting material by treatment with silica gel or equivalent, including, for example, aluminum oxide, to remove monomer oxidation products. However, the catalysts of this invention can polymerize less pure grades of polycyclic monomers when the appropriate NHC precursors and initiators are employed at the appropriate concentration.

Polymerizations were conducted in argon- or nitrogen flushed test tubes, serum vials, glass bottles, reaction vessels, or the like. In general, the polymerizations were accomplished by adding the initiator, whether in solution or in monomer, to the corresponding NHC in monomer. Mixing of the ingredients was accomplished with a vortex, magnetic stir bar, static, mechanical, or impingement mixing. The reaction mixtures were maintained at ambient temperature or heat at constant temperature with heating baths or hot surfaces. Gel times ($t_{gel}$) were estimated by observing the initial viscosity change where the mixture changed from a flowable to a nonflowable mass or, about the time that the polycyclic olefin provided a "string gel" when a rod was inserted into the mix and slowly removed. This was often evident by the observation that the magnetic stir bar stopped stirring due to the viscosity increase of the polymerizing mass. The polymerization temperature ($Tt_{gel}$) at the gel point was also recorded. The time to particular exotherm temperatures, i.e., $t_{100°\,C.}$ or $t_{200°\,C.}$, were recorded when the polymerization exotherm raised the temperature of the polymerizing mass to that temperature, and to the maximum temperature ($T_{max}$) of the polymerization. The maximum temperature ($T_{max}$) of the polymerization was also recorded. The residual monomer level in the polymer samples was obtained by thermogravimetric analysis (TGA) or extraction and quantified using capillary gas chromatography.

Initiator Identities

Ru 575

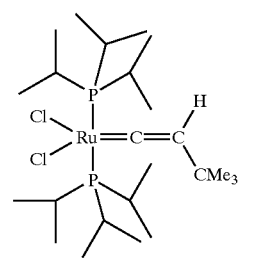

Ru 595

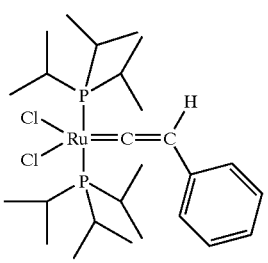

Ru 716

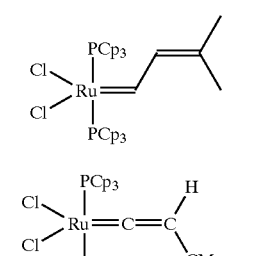

Ru 731

Ru 751

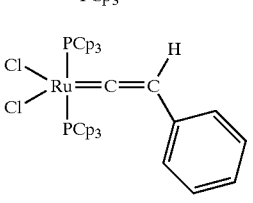

-continued

Ru 779

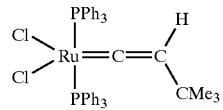

Ru 799

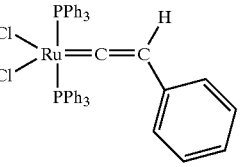

Ru 801

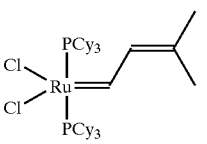

Ru 815

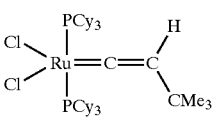

Ru 823

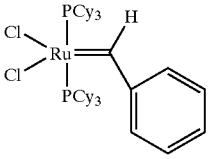

Ru 835

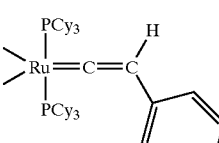

Ru 801(B)

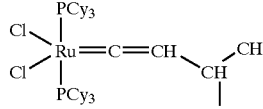

Ru 801(C)

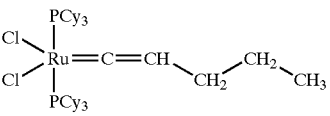

Ru 815(B)

Ru 843

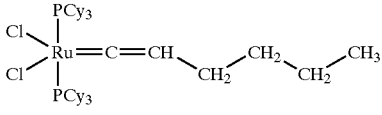

Ru 831

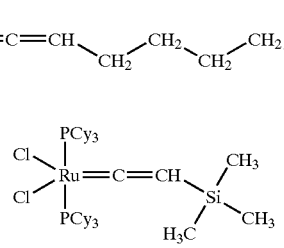

Example 1

A 50 g mass of DCPD (containing 8 wt % trimerized DCPD) was polymerized using Ru 716=0.0361 g in the presence of s-ImesHCCl$_3$=0.0215 g at a DCPD:Ru:s-ImesHCCl$_3$ reactant ratio of (7500:1:1) by heating the mixture to a starting temperature of 49° C.
Result: Time to reach maximum temperature (T$_{max}$)=81 seconds. T$_{max}$=227° C. Conversion measured by thermogravimetric analysis (TGA)=97.35%. Glass transition temperature measured by thermal mechanical analysis (TMA)=154° C. % Residual monomer (toluene extraction at room temperature)=0.51%.

Example 2

A 50 g mass of DCPD was polymerized using Ru 716=0.00677 g in the presence of s-ImesHCCl$_3$=0.0041 g at a DCPD:Ru:s-ImesHCCl$_3$ reactant ratio of (40,000:1:1) by heating the mixture to a starting temperature of 49° C.
Result: Time to reach maximum temperature (T$_{max}$)=510 seconds. T$_{max}$=192° C. Conversion measured by thermogravimetric analysis (TGA) performed under nitrogen @ 400° C.=87.53%. Glass transition temperature measured by thermal mechanical analysis (TMA)=105° C. % Residual monomer (toluene extraction at room temperature)=9.74%.

Example 3

A 50 g mass of DCPD (containing 8 wt % trimerized DCPD) was polymerized using Ru 716=0.0090 g in the presence of s-ImesHCCl$_3$=0.0054 g at a DCPD:Ru:s-ImesHCCl$_3$ reactant ratio of (30,000:1:1) by heating the mixture to a starting temperature of 50° C.
Result: Time to reach maximum temperature (T$_{max}$)=312 seconds. T$_{max}$=205° C. Conversion measured by TGA performed under nitrogen @ 400° C.=90.95%. Glass transition temperature measured by thermal mechanical analysis (TMA)=117° C. % Residual monomer (toluene extraction at room temperature)=6.94%.

Example 4

A 50 g mass of DCPD (containing 8 wt % trimerized DCPD) was polymerized using Ru 716=0.0361 g in the absence of s-ImesHCCl$_3$ at a DCPD:Ru:s-ImesHCCl$_3$ reactant ratio of (7,500:1:0) by heating the mixture to a starting temperature of 48.0° C.
Result: Time to reach maximum temperature (T$_{max}$)=42.5 seconds. T$_{max}$=192° C. Conversion measured by thermogravimetric analysis (TGA) performed under nitrogen @ 400° C.=82.42%. Glass transition temperature measured by thermal mechanical analysis (TMA)=68° C. % Residual monomer (toluene extraction at room temperature)=15.51%.

Example 5

A 50 g mass of DCPD (containing 8 wt % trimerized DCPD) was polymerized using Ru 716=0.00677 g in the presence of s-ImesHCCl$_3$=0.0041 g at a DCPD:Ru:s-ImesHCCl$_3$ reactant ratio of (30,000:1:2) by heating the mixture to a starting temperature of 49° C.
Result: Time to reach maximum temperature (T$_{max}$)=121 seconds. T$_{max}$=229° C. Conversion measured by thermogravimetric analysis (TGA) performed under nitrogen @ 400° C.=95.65%. Glass transition temperature measured by thermal mechanical analysis (TMA)=145° C. % Residual monomer (toluene extraction at room temperature)=1.57%.

Example 6

A 50 g mass of DCPD (containing 8 wt % trimerized DCPD) was polymerized using Ru 716=0.0088 g in the presence of s-ImesHCCl$_3$=0.0209 g at a DCPD:Ru:s-ImesHCCl$_3$ reactant ratio of (30,000:1:4) by heating the mixture to a starting temperature of 49° C.
Result: Time to reach maximum temperature (T$_{max}$)=120 seconds. T$_{max}$=222° C. Conversion measured by TGA performed under nitrogen @ 400° C.=96.98%. Glass transition temperature measured by thermal mechanical analysis (TMA)=146° C. % Residual monomer (toluene extraction at room temperature)=1.10%.

Example 7

A 50 g mass of DCPD (containing 8 wt % trimerized DCPD) was polymerized using Ru 716=0.00677 g in the presence of s-ImesHCCl$_3$=0.0041 g at a DCPD:Ru:s-ImesHCCl$_3$ reactant ratio of (30,000:1:2) by heating the mixture to a starting temperature of 29.5° C.
Result: Time to reach maximum temperature (T$_{max}$)=715 seconds. T$_{max}$=203° C. Conversion measured by TGA performed under nitrogen @ 400° C.=97.40%. Glass transition temperature measured by thermal mechanical analysis (TMA)=155° C. % Residual monomer (toluene extraction at room temperature)=0.61%.

Example 8

A 50 g mass of DCPD (containing 8 wt % trimerized DCPD) was polymerized using Ru 716=0.00677 g in the presence of s-ImesHCCl$_3$=0.0164 g at a DCPD:Ru:s-ImesHCCl$_3$ reactant ratio of (40,000:1:4) by heating the mixture to a starting temperature of 50° C.
Result: Time to reach maximum temperature (T$_{max}$)=151 seconds. T$_{max}$=220° C. Conversion measured by TGA performed under nitrogen @ 400° C.=95.51%.

Example 9

A 50 g mass of DCPD (containing 24 wt % trimerized DCPD) was polymerized using Ru 801=0.0372 g at a DCPD:Ru reactant ratio of (7500:1) by heating the mixture to a starting temperature of 30.2° C. The DCPD monomer was sparged with argon for approximately 30 minutes, but not filtered prior to polymerization.
Result: Time to reach maximum temperature (T$_{max}$)=280 seconds. T$_{max}$=200.1° C. % Residual monomer (toluene extraction at room temperature)=3.03%. % Weight loss at 300° C. and 400° C. measured by thermogravimetric analysis (TGA))=2.85% and 4.51%. Glass transition temperature measured by thermal mechanical analysis (TMA)=153° C.

Example 10

A 50 g mass of DCPD (containing 24 wt % trimerized DCPD) was polymerized using Ru 801=0.0372 g in the presence of s-ImesHCCl$_3$=0.0396 g at a DCPD:Ru:s-ImesHCCl$_3$ reactant ratio of (7500:1:2) by heating the mixture to a starting temperature of 30.0° C. The DCPD monomer was sparged with argon for approximately 30 minutes, but not filtered prior to polymerization.
Result: Time to reach maximum temperature (T$_{max}$)=273 seconds. T$_{max}$=207.6° C. % Residual monomer (toluene extraction at room temperature)=0.06%. % Weight loss at 300° C. and 400° C. measured by thermogravimetric analysis (TGA))=1.05% and 2.17%. Glass transition temperature measured by thermal mechanical analysis (TMA)=192° C.

Example 11

A 50 g mass of DCPD (containing 24 wt % trimerized DCPD) was polymerized using Ru 801=0.0093 g at a DCPD:Ru reactant ratio of (30,000:1) by heating the mixture to a starting temperature of 30.4° C. The DCPD monomer was sparged with argon for approximately 30 minutes and filtered with activated $Al_2O_3$ prior to polymerization.
Result: Time to reach maximum temperature $(T_{max})$=593 seconds. $T_{max}$=164.2° C. % Residual monomer (toluene extraction at room temperature)=0.06%. % Weight loss at 300° C. and 400° C. measured by thermogravimetric analysis (TGA))=17.9% and 21.6%. Glass transition temperature measured by thermal mechanical analysis (TMA)=86° C.

Example 12

A 50 g mass of DCPD (containing 24 wt % trimerized DCPD) was polymerized using Ru 801=0.0093 g in the presence of s-ImesHCCl$_3$=0.0099 g at a DCPD:Ru:s-ImesHCCl$_3$ reactant ratio of (30,000:1:2) by heating the mixture to a starting temperature of 30.3° C. The DCPD monomer was sparged with argon for approximately 30 minutes and filtered with activated $Al_2O_3$ prior to polymerization.
Result: Time to reach maximum temperature $(T_{max})$=588 seconds. $T_{max}$=199.9° C. % Residual monomer (toluene extraction at room temperature)=0.78%. % Weight loss at 300° C. and 400° C. measured by thermogravimetric analysis (TGA))=1.35% and 2.56%. Glass transition temperature measured by thermal mechanical analysis (TMA)=178° C.

Example 13

A 50 g mass of DCPD (containing 24 wt % trimerized DCPD) was polymerized using Ru 835=0.0388 g in the presence of s-ImesHCCl$_3$=0.0396 g at a DCPD:Ru:s-ImesHCCl$_3$ reactant ratio of (7500:1:2) by heating the mixture to a starting temperature of 53.7° C. The DCPD monomer was sparged with argon for approximately 30 minutes and filtered with activated $Al_2O_3$ prior to polymerization.
Result: Time to reach maximum temperature $(T_{max})$=239 seconds. $T_{max}$=219.6° C. % Residual monomer (toluene extraction at room temperature)=1.64%. % Weight loss at 300° C. and 400° C. measured by thermogravimetric analysis (TGA))=2.41% and 3.99%. Glass transition temperature measured by thermal mechanical analysis (TMA)=168° C.

Example 14

A 50 g mass of DCPD (containing 24 wt % trimerized DCPD) was polymerized using Ru 835=0.0097 g in the presence of s-ImesHCCl$_3$=0.0099 g at a DCPD:Ru:s-ImesHCCl$_3$ reactant ratio of (30,000:1:2) by heating the mixture to a starting temperature of 52.1° C. The DCPD monomer was sparged with argon for approximately 30 minutes and filtered with activated $Al_2O_3$ prior to polymerization.
Result: Time to reach maximum temperature $(T_{max})$=484 seconds. $T_{max}$=202.6° C. % Residual monomer (toluene extraction at room temperature)=5.24%. % Weight loss at 300° C. and 400° C. measured by thermogravimetric analysis (TGA))=4.64% and 7.30%. Glass transition temperature measured by thermal mechanical analysis (TMA)=149° C.

Example 15

A 50 g mass of DCPD (containing 24 wt % trimerized DCPD) was polymerized using Ru 823=0.0048 g in the presence of s-ImesHCCl$_3$=0.0049 g at a DCPD:Ru:s-ImesHCCl$_3$ reactant ratio of (60,000:1:2) by heating the mixture to a starting temperature of 33.8° C. The DCPD monomer was sparged with argon for approximately 30 minutes and filtered with activated $Al_2O_3$ prior to polymerization.
Result: Time to reach maximum temperature $(T_{max})$=134 seconds. $T_{max}$=204.6° C. % Residual monomer (toluene extraction at room temperature)=1.84%. % Weight loss at 300° C. and 400° C. measured by thermogravimetric analysis (TGA))=1.99% and 3.56%. Glass transition temperature measured by thermal mechanical analysis (TMA)=165° C.

Example 16

A 50 g mass of DCPD (containing 24 wt % trimerized DCPD) was polymerized using Ru 823=0.0048 g at a DCPD:Ru reactant ratio of (60,000:1) by heating the mixture to a starting temperature of 33.2° C. The DCPD monomer was sparged with argon for approximately 30 minutes and filtered with activated $Al_2O_3$ prior to polymerization.
Result: Time to reach maximum temperature $(T_{max})$=182 seconds. $T_{max}$=158.1° C. % Residual monomer (toluene extraction at room temperature)=20.35%. % Weight loss at 300° C. and 400° C. measured by thermogravimetric analysis (TGA))=20.70% and 24.71%. Glass transition temperature measured by thermal mechanical analysis (TMA)=72° C.

Example 17

A 50 g mass of DCPD (containing 24 wt % trimerized DCPD) was polymerized using Ru 823=0.0048 g in the presence of s-ImesHCCl$_3$=0.0099 g at a DCPD:Ru:s-ImesHCCl$_3$ reactant ratio of (60,000:1:4) by heating the mixture to a starting temperature of 32.2° C. The DCPD monomer was sparged with argon for approximately 30 minutes and filtered with activated $Al_2O_3$ prior to polymerization.
Result: Time to reach maximum temperature $(T_{max})$=162 seconds. $T_{max}$=188.8° C. % Residual monomer (toluene extraction at room temperature)=6.54%. % Weight loss at 300° C. and 400° C. measured by thermogravimetric analysis (TGA))=5.20% and 7.82%. Glass transition temperature measured by thermal mechanical analysis (TMA)=130° C.

Example 18

A 50 g mass of DCPD (containing 24 wt % trimerized DCPD) was polymerized using Ru 815=0.0379 g in the presence of s-ImesHCCl$_3$=0.0396 g at a DCPD:Ru:s-ImesHCCl$_3$ reactant ratio of (7,500:1:2) by heating the mixture to a starting temperature of 47.9° C. The DCPD monomer was sparged with argon for approximately 30 minutes and filtered with activated $Al_2O_3$ prior to polymerization.
Result: Time to reach maximum temperature $(T_{max})$=228 seconds. $T_{max}$=219.3° C. Glass transition temperature measured by thermal mechanical analysis (TMA)=191° C.

Example 19

A 50 g mass of DCPD (containing 24 wt % trimerized DCPD) was polymerized using Ru 815=0.0095 g in the presence of s-ImesHCCl$_3$=0.0099 g at a DCPD:Ru:s-ImesHCCl$_3$ reactant ratio of (30,000:1:2) by heating the mixture to a starting temperature of 50.2° C. The DCPD monomer was sparged with argon for approximately 30 minutes and filtered with activated $Al_2O_3$ prior to polymerization.

Result: Time to reach maximum temperature ($T_{max}$)=239 seconds. $T_{max}$=217.2° C. % Residual DCPD (solvent extraction)=0.98%. Glass transition temperature measured by thermal mechanical analysis (TMA)=175° C.

Example 20

A 50 g mass of DCPD (containing 24 wt % trimerized DCPD) was polymerized using Ru 716=0.0333 g in the presence of s-ImesHCCl$_3$=0.0099 g at a DCPD:Ru:s-ImesHCCl$_3$ reactant ratio of (7,500:1:0.5) by heating the mixture to a starting temperature of 31.6° C. The DCPD monomer was sparged with argon for approximately 30 minutes and filtered with activated Al$_2$O$_3$ prior to polymerization.
Result: Time to reach maximum temperature ($T_{max}$)=193 seconds. $T_{max}$=210.1° C. % Residual DCPD (solvent extraction)=0.17%. Glass transition temperature measured by thermal mechanical analysis (TMA)=189° C.

Example 21

A 50 g mass of DCPD (containing 24 wt % trimerized DCPD) was polymerized using Ru 779=0.0362 g in the presence of s-ImesHCCl$_3$=0.0396 g at a DCPD:Ru:s-ImesHCCl$_3$ reactant ratio of (7,500:1:2) by heating the mixture to a starting temperature of 75° C. The DCPD monomer was sparged with argon for approximately 30 minutes and filtered with activated Al$_2$O$_3$ prior to polymerization.
Result: Time to reach maximum temperature ($T_{max}$)=421 seconds. $T_{max}$=205° C.

Example 22

A 75 g mass of DCPD (containing 24 wt % trimerized DCPD) was polymerized using Ru 731=0.0191 g in the presence of s-ImesHCCl$_3$=0.0223 g at a DCPD:Ru:s-ImesHCCl$_3$ reactant ratio of (20,000:1:2) by heating the mixture to a starting temperature of 50.3° C. The DCPD monomer was sparged with argon for approximately 30 minutes and filtered with activated Al$_2$O$_3$ prior to polymerization.
Result: Time to reach maximum temperature ($T_{max}$)=442 seconds. $T_{max}$=227.9° C. % Residual DCPD (solvent extraction)=0.68%. Average Tg (via TMA)=180.07° C.

Example 23

A 75 g mass of DCPD (containing 24 wt % trimerized DCPD) was polymerized using Ru 751=0.0393 g in the presence of s-ImesHCCl$_3$=0.0445 g at a DCPD:Ru:s-ImesHCCl$_3$ reactant ratio of (10,000:1:2) by heating the mixture to a starting temperature of 50.1° C. The DCPD monomer was sparged with argon for approximately 30 minutes and filtered with activated Al$_2$O$_3$ prior to polymerization.
Result: Time to reach maximum temperature ($T_{max}$)=1791 seconds. $T_{max}$=218.1° C. % Residual DCPD (solvent extraction)=1.82%. Average Tg (via TMA)=167.71° C.

Example 24

A 75 g mass of DCPD (containing 24 wt % trimerized DCPD) was polymerized using Ru 801(C)=0.0209 g in the presence of s-ImesHCCl$_3$=0.0111 g at a DCPD:Ru:s-ImesHCCl$_3$ reactant ratio of (20,000:1:1) by heating the mixture to a starting temperature of 50.2° C. The DCPD monomer was sparged with argon for approximately 30 minutes and filtered with activated Al$_2$O$_3$ prior to polymerization.
Result: Time to reach maximum temperature ($T_{max}$)=328 seconds. $T_{max}$=217.1° C. % Residual DCPD (solvent extraction)=4.17%. Average Tg (via TMA)=142.62° C.

Example 25

A 75 g mass of DCPD (containing 24 wt % trimerized DCPD) was polymerized using Ru 801(C)=0.0209 g in the presence of s-ImesHCCl$_3$=0.0223 g at a DCPD:Ru:s-ImesHCCl$_3$ reactant ratio of (20,000:1:2) by heating the mixture to a starting temperature of 49.5° C. The DCPD monomer was sparged with argon for approximately 30 minutes and filtered with activated Al$_2$O$_3$ prior to polymerization.
Result: Time to reach maximum temperature ($T_{max}$)=310 seconds. $T_{max}$=218.9° C. % Residual DCPD (solvent extraction)=3.83%. Average Tg (via TMA)=147.46° C.

Example 26

A 75 g mass of DCPD (containing 24 wt % trimerized DCPD) was polymerized using Ru 831=0.0434 g in the presence of s-ImesHCCl$_3$=0.0223 g at a DCPD:Ru:s-ImesHCCl$_3$ reactant ratio of (10,000:1:1) by heating the mixture to a starting temperature of 50.3° C. The DCPD monomer was sparged with argon for approximately 30 minutes and filtered with activated Al$_2$O$_3$ prior to polymerization.
Result: Time to reach maximum temperature ($T_{max}$)=645 seconds. $T_{max}$=218.1° C. % Residual DCPD (solvent extraction)=2.34%. Average Tg (via TMA)=159.87° C.

Example 27

A 75 g mass of DCPD (containing 24 wt % trimerized DCPD) was polymerized using Ru 831=0.0434 g in the presence of s-ImesHCCl$_3$=0.0223 g at a DCPD:Ru:s-ImesHCCl$_3$ reactant ratio of (20,000:1:2) by heating the mixture to a starting temperature of 50.1° C. The DCPD monomer was sparged with argon for approximately 30 minutes and filtered with activated Al$_2$O$_3$ prior to polymerization.
Result: Time to reach maximum temperature ($T_{max}$)=869 seconds. $T_{max}$=213.2° C. % Residual DCPD (solvent extraction)=2.87%. Average Tg (via TMA)=156.12° C.

Example 28

A 75 g mass of DCPD (containing 24 wt % trimerized DCPD) was polymerized using Ru 801(B)=0.0209 g in the presence of s-ImesHCCl$_3$=0.0223 g at a DCPD:Ru:s-ImesHCCl$_3$ reactant ratio of (20,000:1:2) by heating the mixture to a starting temperature of 50.1° C. The DCPD monomer was sparged with argon for approximately 30 minutes and filtered with activated Al$_2$O$_3$ prior to polymerization.
Result: Time to reach maximum temperature ($T_{max}$)=249 seconds. $T_{max}$=226.6° C. % Residual DCPD (solvent extraction)=1.13%. Average Tg (via TMA)=164.28° C.

Example 29

A 75 g mass of DCPD (containing 24 wt % trimerized DCPD) was polymerized using Ru 815(B)=0.0213 g in the presence of s-ImesHCCl$_3$=0.0223 g at a DCPD:Ru:s-ImesHCCl$_3$ reactant ratio of (20,000:1:2) by heating the mixture to a starting temperature of 49.6° C. The DCPD monomer was sparged with argon for approximately 30 minutes and filtered with activated Al$_2$O$_3$ prior to polymerization.

Result: Time to reach maximum temperature ($T_{max}$)=303 seconds. $T_{max}$=220.1° C. % Residual DCPD (solvent extraction)=3.62%. Average Tg (via TMA)=145.41° C.

Example 30

A 75 g mass of DCPD (containing 24 wt % trimerized DCPD) was polymerized using Ru 843=0.0220 g in the presence of s-ImesHCCl$_3$=0.0223 g at a DCPD:Ru:s-ImesHCCl$_3$ reactant ratio of (20,000:1:2) by heating the mixture to a starting temperature of 49.4° C. The DCPD monomer was sparged with argon for approximately 30 minutes and filtered with activated Al$_2$O$_3$ prior to polymerization.
Result: Time to reach maximum temperature ($T_{max}$)=282 seconds. $T_{max}$=220.8° C. % Residual DCPD (solvent extraction)=2.90%. Average Tg (via TMA)=140.10° C.

Example 31

A 75 g mass of DCPD (containing 24 wt % trimerized DCPD) was polymerized using Ru 815=0.0213 g in the presence of s-ImesHCCl$_3$=0.0223 g at a DCPD:Ru:s-ImesHCCl$_3$ reactant ratio of (20,000:1:2) by heating the mixture to a starting temperature of 50.4° C. The DCPD monomer was sparged with argon for approximately 30 minutes and filtered with activated Al$_2$O$_3$ prior to polymerization.
Result: Time to reach maximum temperature ($T_{max}$)=245 seconds. $T_{max}$=230.9° C. % Residual DCPD (solvent extraction)=0.72%. Average Tg (via TMA)=183.6° C.

Example 32

A 75 g mass of DCPD (containing 24 wt % trimerized DCPD) was polymerized using Ru 815=0.0213 g at a DCPD:Ru reactant ratio of (20,000:1) by heating the mixture to a starting temperature of 49.7° C. The DCPD monomer was sparged with argon for approximately 30 minutes and filtered with activated Al$_2$O$_3$ prior to polymerization.
Result: Time to reach maximum temperature ($T_{max}$)=200 seconds. $T_{max}$=192.4° C. % Residual DCPD (solvent extraction)=13.71%. Average Tg (via TMA)=84.47° C.

Example 33

A 75 g mass of DCPD (containing 24 wt % trimerized DCPD) was polymerized using Ru 815(B)=0.0213 g at a DCPD:Ru reactant ratio of (20,000:1) by heating the mixture to a starting temperature of 49.9° C. The DCPD monomer was sparged with argon for approximately 30 minutes and filtered with activated Al$_2$O$_3$ prior to polymerization.
Result: Time to reach maximum temperature ($T_{max}$)=264 seconds. $T_{max}$=165.2° C. % Residual DCPD (solvent extraction)=26.16%. Average Tg (via TMA)=44.56° C.

Example 34

A 75 g mass of DCPD (containing 24 wt % trimerized DCPD) was polymerized using Ru 801(C)=0.0209 g at a DCPD:Ru reactant ratio of (20,000:1) by heating the mixture to a starting temperature of 49.5° C. The DCPD monomer was sparged with argon for approximately 30 minutes and filtered with activated Al$_2$O$_3$ prior to polymerization.
Result: Time to reach maximum temperature ($T_{max}$)=334 seconds. $T_{max}$=165.1° C. % Residual DCPD (solvent extraction)=26.12%. Average Tg (via TMA)=42.30° C.

Example 35

A 75 g mass of DCPD (containing 24 wt % trimerized DCPD) was polymerized using Ru 801(B)=0.0209 g at a DCPD:Ru reactant ratio of (20,000:1) by heating the mixture to a starting temperature of 51.1° C. The DCPD monomer was sparged with argon for approximately 30 minutes and filtered with activated Al$_2$O$_3$ prior to polymerization.
Result: Time to reach maximum temperature ($T_{max}$)=170 seconds. $T_{max}$=183.6° C. % Residual DCPD (solvent extraction)=18.36%. Average Tg (via TMA)=66.06° C.

Example 36

A 75 g mass of DCPD (containing 24 wt % trimerized DCPD) was polymerized using Ru 843=0.0220 g at a DCPD:Ru reactant ratio of (20,000:1) by heating the mixture to a starting temperature of 49.7° C. The DCPD monomer was sparged with argon for approximately 30 minutes and filtered with activated Al$_2$O$_3$ prior to polymerization.
Result: Time to reach maximum temperature ($T_{max}$)=267 seconds. $T_{max}$=169.8° C. % Residual DCPD (solvent extraction)=24.58%. Average Tg (via TMA)=42.01° C.

Example 37

A 75 g mass of Hexylnorbornene was polymerized using Ru 815=0.0171 g in the presence of s-ImesHCCl$_3$=0.0179 g at a H$_x$N:Ru:s-ImesHCCl$_3$ reactant ratio of (20,000:1:2) by heating the mixture to a-starting temperature of 50.1° C.
Result: Time to reach maximum temperature ($T_{max}$)=198 seconds. $T_{max}$=172.2° C.

Example 38

50.0 g of 1,3-Bis-(2,4,6-trimethylphenyl)imidazolinium chloride was added to a 1000 mL single neck round bottom flask containing a Teflon-coated stirbar. 15.2 g of Lithium tert-butoxide (1.3 mol equivalents of Lithium tert-butoxide to 1,3-Bis-(2,4,6-trimethylphenyl)imidazolinium chloride) was added to the 1000 mL flask. 190 mL of anhydrous Hexanes was added to the 1000 mL flask and the flask was capped with a septum and the headspace was purged with argon for 15 minutes with stirring. This mixture was stirred for 2 hours at room temperature.

After 2 hours the septum on the 1000 mL flask was replaced with a 250 mL addition funnel. 250 mL of CHCl$_3$ was added to the addition funnel and the funnel was capped with a septum and purged with argon for 5 minutes. After the 250 mL of CHCl$_3$ was added dropwise to the reaction mixture in the 1000 mL flask an additional 130 mL of CHCl$_3$ was added to the addition funnel and the funnel was capped with a septum and purged with argon for 5 minutes. The additional 130 mL of CHCl$_3$ was added dropwise to the reaction mixture in the 1000 mL flask with stirring. A total of 380 mL of CHCl$_3$ was added dropwise to the 1000 mL flask at room temperature under an atmosphere of argon with stirring. Once the 380 mL of CHCl$_3$ was added to the 1000 mL flask the additional funnel was removed from the flask and the flask was capped with a septum. The headspace of the flask was purged with argon for 15 minutes. The reaction mixture was stirred for 24 hours under an atmosphere of argon to yield an off-white solution.

This off-white solution is cooled to 0° C. and then washed with saturated NH$_4$Cl$_{(aq)}$ (4×200 mL) in a separatory funnel at 22–25° C. The organic layer was then washed with saturated NaCl$_{(aq)}$ (2×200 mL) in a separatory funnel at 22–25° C. The organic layer was then placed in a single neck round bottom flask and the excess chloroform was removed in vacuo to yield the crude product as a powdery off-white solid. The off-white solid was washed with a minimal amount of cold methanol (0° C.) and filtered to give 52.5 g of 1,3-dimesityl-2-(trichloromethyl)imidazolidine (62.1 g theoretical yield) as a white to off-white crystalline powder in 85% yield.

Example 39

Preparation of Glyoxal-bis-(2,4,6-trimethylphenyl)imine

A 125 mL clear glass bottle with a Teflon-lined cap and coated stirring bar was charged with 2-propanol (25% w/w aqueous solution, 32.4 g), 2,4,6-trimethylaniline (10.0 g, 74.0 mmol), and glyoxal (40% w/w aqueous solution, 5.3 g, 37 mmol). The glyoxal was added last, and within minutes the reaction began to evolve a yellow color in the mother liquor concomitant with the precipitation of a yellow solid. The mixture was stirred for 24 hours at ambient temperature, after which time the reaction mixture was thick with precipitate. The product was isolated by filtration and washed with methanol 2×25 mL. Vacuum drying afforded the product as a canary yellow solid. Yield: 10.2 g (94%).

Preparation of N,N'Bis-(2,4,6-trimethylphenylamino)ethane

A dry, 100 mL Schlenk flask with a Teflon-coated stirbar was charged with glyoxal-bis-(2,4,6-trimethylphenyl)imine (10.0 g, 34.2 mmol). The flask was evacuated to remove air and backfilled with argon. Toluene (Aldrich anhydrous grade, 20 mL) was then added, and the reaction vessel was placed in a water ice bath.

Sodium dihydridobis(2-methoxyethoxy)aluminate, (70% w/w in toluene, d 1.036, 12.5 mL, 44.8 mmol) was charged into a dry, argon-purged addition funnel and then added dropwise to the stirred yellow slurry of bisimine over approximately 15–20 min. The reaction was fast and quite exothermic. Over the course of the sodium dihydridobis(2-methoxyethoxy)aluminate addition, the slurry gradually homogenized until all solids were dissolved and the yellow color of the starting bisimine had discharged, yielding a clear to slightly opaque amber solution. The reaction flask was removed from the bath and allowed to warm to room temperature with stirring overnight.

Prior to workup, it was observed that the initially clear reaction mixture had become opaque. Aqueous sodium hydroxide (25% w/w, 5 g) was added to the resulting off-white slurry until all solids had dissolved. This clear biphasic mixture was then transferred to a separatory funnel, and the (upper) organic layer was removed. The aqueous fraction was then washed with toluene 3×25 mL. The combined organic extracts were concentrated by rotary evaporation to yield 10.2 g (90%) of N,N'-bis-(2,4,6-trimethylphenylamino)ethane, 99% pure by gas chromatography, as a brown oil which crystallized over time.

Preparation of N,N'-Bis-(2,4,6-trimethylphenylamino)ethane Dihydrochloride

A 250 mL Erlenmeyer flask containing a Teflon-coated stirring bar was charged with N,N'-Bis-(2,4,6-trimethylphenylamino)ethane (26.6 g, 89.7 mmol), toluene (7 g), 2-propanol (64 mL), and deionized water (64 mL). The vessel was cooled in a water ice bath, and HCl (12 M, 21 mL, 252 mmol) was added dropwise over approximately 0.5 hour. The reaction mixture quickly thickened with white precipitate as the acid was added, and heat was evolved. After the addition, the reaction was allowed to warm to ambient temperature and left to stir overnight. The product was isolated by filtration from the pale pink mother liquor and washed with successive portions of methanol (3×50 mL), and hexanes (1×100 mL), followed by vacuum drying to yield 31.3 g (94%) of N,N'-Bis-(2,4,6-trimethylphenylamino)ethane dihydrochloride as a white to off-white, microcrystalline powder.

Preparation of 1,3-Bis-(2,4,6-trimethylphenyl)imidazolinium Chloride

A 500 mL three-neck round bottom flask, containing a Teflon-coated stirbar and fitted with an internal thermometer and a short path distillation head, was charged with bis-(2,4,6-trimethylphenylamino)ethane dihydrochloride (20.18 g, 54.63 mmol) and triethylorthoformate (200 mL). Acetic acid (98%, ca. 4 drops from a Pasteur pipette) was added, and the reaction vessel was placed in a 130° C. oil bath. As the beige slurry was heated and stirred, a water white liquid began to distill away from the reaction mixture which itself had taken on a pink tint. Heating was continued until distillation ceased, about 4 hours. The final temperature of the reaction mixture was 120° C. After the reaction mixture had cooled to ambient temperature, the pink color had discharged. The solid product was isolated by filtration and washed with hexanes (3×100 mL). Vacuum drying afforded 18.21 g (97%) of 1,3-Bis-(2,4,6-trimethylphenyl)imidazolinium chloride as a white, crystalline powder.

Example 40

A 75 g mass of a monomer mixture, prepared by mixing together 67.5 g of DCPD (containing 24 wt % trimerized DCPD) and 7.5 g of hexylnorbornene, was polymerized using Ru 815=0.0209 g in the presence of s-ImesHCCl$_3$=0.0218 g at a DCPD:Ru:s-ImesHCCl$_3$ reactant ratio of (20,000:1:2) and H$_x$N:Ru:s-ImesHCCl$_3$ reactant ratio of (20,000:1:2), by heating the mixture to a starting temperature of 50.0° C.

Result: Time to reach maximum temperature (T$_{max}$)=218 seconds. T$_{max}$=219.2° C.

Example 41

A 75 g mass of a monomer mixture, prepared by mixing together 67.5 g of DCPD (containing 24 wt % trimerized DCPD) and 7.5 g of hexylnorbornene, was polymerized using Ru 815=0.0209 g at a DCPD:Ru reactant ratio of (20,000:1) and H$_x$N:Ru reactant ratio of (20,000:1), by heating the mixture to a starting temperature of 51.3° C.

Result: Time to reach maximum temperature (T$_{max}$)=194 seconds. T$_{max}$=190.9° C.

Example 42

A 75 g mass of a monomer mixture, prepared by mixing together 56.25 g of DCPD (containing 24 wt % trimerized DCPD) and 18.75 g of hexylnorbornene, was polymerized using Ru 823=0.0136 g in the presence of s-ImesHCCl$_3$=0.0141 g at a DCPD:Ru:s-ImesHCCl$_3$ reactant ratio of (30,000:1:2) and H$_x$N:Ru:s-ImesHCCl$_3$ reactant ratio of (30,000:1:2), by heating the mixture to a starting temperature of 27.6° C.

Result: Time to reach maximum temperature (T$_{max}$)=192 seconds. T$_{max}$=199.3° C.

Example 43

A 75 g mass of a monomer mixture, prepared by mixing together 56.25 g of DCPD (containing 24 wt % trimerized DCPD) and 18.75 g of hexylnorbornene, was polymerized using Ru 823=0.0136 g at a DCPD:Ru reactant ratio of (30,000:1) and H$_x$N:Ru reactant ratio of (30,000:1), by heating the mixture to a starting temperature of 27.7° C.

Result: Time to reach maximum temperature (T$_{max}$)=155 seconds. T$_{max}$=171.4° C.

Example 44

A 75 g mass of Hexylnorbornene was polymerized using Ru 823=0.0115 g in the presence of s-ImesHCCl$_3$=0.0119 g at a H$_x$N:Ru:s-ImesHCCl$_3$ reactant ratio of (30,000:1:2) by heating the mixture to a starting temperature of 28.3° C.

Result: Time to reach maximum temperature (T$_{max}$)=175 seconds. T$_{max}$=155.7° C.

What is claimed is:

1. A process for converting a less active or slower to initiate catalyst system to a higher activity catalyst system, the process comprising contacting a protected N-heterocyclic carbene with a metathesis initiator and an olefin in the presence of energy, wherein the protected N-heterocyclic carbene is of the formula NHC—$X^2$—Y, NHC is any N-heterocyclic carbene ligand, and $X^2$—Y is any moiety that is released in the presence of energy.

2. The process of claim 1 wherein the protected N-heterocyclic carbene is of the formula:

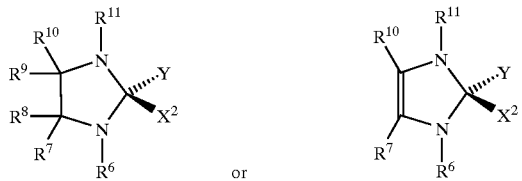

wherein $R^6$, $R^7$, $R^8$, $R^9$, $R^{10}$ and $R^{11}$ are each independently hydrogen or a substituted or unsubstituted substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$-$C_{20}$ alkylsulfinyl;

$X^2$ is selected from the group consisting of hydrogen, Si, Sn, Li, Na, $MgX^3$ and acyl, wherein $X^3$ is any halogen; and Y is selected from the group consisting of $CCl_3$; $CH_2SO_2Ph$; $C_6F_5$; $OR^{21}$; and $N(R^{22})(R^{23})$, wherein $R^{21}$ is selected from the group consisting of Me, $C_2H_5$, i-$C_3H_7$, $CH_2CMe_3$, $CMe_3$, $C_6H_{11}$ (cyclohexyl), $CH_2Ph$, $CH_2$norbornyl, $CH_2$norbornenyl, $C_6H_5$, 2,4,6-$(CH_3)_3$ $C_6H_2$ (mesityl), 2,6-i-$Pr_2C_6H_2$, 4-Me-$C_6H_4$ (tolyl), and 4-Cl—$C_6H_4$; and wherein $R^{22}$ and $R^{23}$ are each independently selected from the group consisting of Me, $C_2H_5$, i-$C_3H_7$, $CH_2CMe_3$, $CMe_3$, $C_6H_{11}$ (cyclohexyl), $CH_2Ph$, $CH_2$norbornyl, $CH_2$norbornenyl, $C_6H_5$, 2,4,6-$(CH_3)_3C_6H_2$ (mesityl), 2,6-i-$Pr_2C_6H_2$, and 4-Me-$C_6H_4$ (tolyl), 4-Cl—$C_6H_4$).

3. The process of claim 2 wherein the at least one substituent is substituted with one or more substituted or unsubstituted moieties selected from the group consisting of $C_1$–$C_{10}$ alkyl, $C_1$–$C_{10}$ alkoxy, and aryl.

4. The process of claim 3 wherein at least one moiety is substituted with one or more groups selected from the group consisting of halogen, a $C_1$–$C_5$ alkyl, $C_1$–$C_5$ alkoxy, and phenyl.

5. The process of claim 2 wherein at least one of the $R^6$, $R^7$, $R^8$, $R^9$, $R^{10}$ and $R^{11}$ substituent groups includes one or more functional groups selected from the group consisting of hydroxyl, thiol, alcohol, sulfonic acid, phosphine, thioether, ketone, aldehyde, ester, ether, amine, imine, amide, imide, imido, nitro, carboxylic acid, disulfide, carbonate, isocyanate, carbodiimide, carboalkoxy, carbamate, acetal, ketal, boronate, cyano, cyanohydrin, hydrazine, oxime, hydrazide, enamine, sulfone, sulfide, sulfenyl, and halogen.

6. The process of claim 2 wherein $R^7$, $R^8$, $R^9$ and $R^{10}$ are each independently selected from the group consisting of hydrogen, methyl, aralkyl, and aryl and $R^6$ and $R^{11}$ are each independently selected from the group consisting of substituted or unsubstituted $C_1$–$C_{10}$ alkyl, $C_1$–$C_{10}$ cycloalkyl, $C_2$–$C_{10}$ alkenyl, aralkyl, and aryl.

7. The process of claim 6 wherein $R^7$, $R^8$, $R^9$ and $R^{10}$ are each hydrogen and $R^6$ and $R^{11}$ substituents are each independently substituted or unsubstituted and are selected from the group consisting of phenyl, vinyl, methyl, isopropyl, tert-butyl, neopentyl, or benzyl.

8. The process of claim 7 wherein the substituent is substituted with one or more moieties selected from the group consisting of $C_1$–$C_5$ alkyl, $C_1$–$C_5$ alkoxy, phenyl, and a functional group.

9. The process of claim 7 wherein $R^6$ and $R^{11}$ are each independently substituted or unsubstituted aryl.

10. The process of claim 2 wherein at least two of $R^6$, $R^7$, $R^8$, $R^9$, $R^{10}$ and $R^{11}$ is linked to form an substituted or unsubstituted, saturated or unsaturated ring structure.

11. The process of claim 1 wherein the NHC—$X^2$—Y is selected from the group consisting of 1,3-dimesityl-2-methoxy-imidazolidine, 1,3-dimesityl-2-(trichloromethyl) imidazolidine, 1,3-dimesityl-2-ethoxy-imidazolidine, 1,3-dimesityl-2-tert-butoxy-imidazolidine, 1,3-dimesityl-2-benzyloxy-imidazolidine, 1,3-diphenyl-2-(trichloromethyl) imidazolidine, 1,3-bis(3-chlorophenyl)-2-(trichloromethyl) imidazolidine, 1,3-bis(4-methylphenyl)-2-(trichloromethyl) imidazolidine, 1,3-bis(4-fluorophenyl)-2-(trichloromethyl) imidazolidine, 1,3-bis(3-methylphenyl)-2-(trichloromethyl) imidazolidine, 1,3-bis(4-chlorophenyl)-2-(trichloromethyl) imidazolidine, 1,3-bis(4-bromophenyl)-2-(trichloromethyl) imidazolidine, 1,3-bis(4-iodophenyl)-2-(trichloromethyl) imidazolidine, 1,3-bis(4-methoxyphenyl)-2-(trichloromethyl)imidazolidine, 1,3-bis(4-ethoxyphenyl)-2-(trichloromethyl)imidazolidine, 1,3-bis(4-ethylphenyl)-2-(trichloromethyl)imidazolidine, 1,3-bis(4-nitrophenyl)-2-(trichloromethyl)imidazolidine, 1,3-bis(3,4-dimethylphenyl)-2-(trichloromethyl)imidazolidine, 1,3-bis (3,5-dichlorophenyl)-2-(trichloromethyl) imidazolidine, 1,3-bis(3,5-dimethylphenyl)-2-(trichloromethyl imidazolidine, 1-(4-chlorophenyl)-3-phenyl-2-(trichloromethyl)imidazolidine, 1,3-bis(4-fluorophenyl)-2-(trichloromethyl)imidazolidine, 1-(4-methoxyphenyl)-3-phenyl-2-(trichloromethyl imidazolidine, 2-(trichloromethyl)-1,3-bis(2,6-dimethyl-4-tert-butylphenyl)imidazolidine, 2-(trichloromethyl)-1,3-bis(2,6-diisopropylphenyl)imidazolidine, 1,3-dimesityl-2-dimethylamino-imidazolidine, 1-(1,3-dimesityl-2-imidazolidinyl)-piperidine, and, 4-(1,3-dimesityl-2-imidazolidinyl)-morpholine.

12. The process of claim 1 wherein the energy is selected from the group consisting of thermal energy, laser, electron beam radiation, gamma radiation, plasma, sound, ultraviolet, and microwave radiation.

13. The process of claim 1 wherein the olefin is cyclic or acyclic.

14. The process of claim 1 wherein the olefin contains more than one polymerizable double bond.

15. The process of claim 1 wherein the olefin is a monocyclic olefin or polycyclic olefin.

16. The process of claim 15 wherein the olefin is a substituted or unsubstituted monocyclic olefin and is selected from the group consisting of cyclopropene, cyclobutene, cyclopentene, methylcyclopentene, cycloheptene, cyclooctene, 5-acetoxycyclooctene, 5-hydroxycyclooctene, cyclooctadiene, cyclotetraene, cyclodecene, and cyclododecene.

17. The process of claim 15 wherein the olefin is a polycyclic olefin and is selected from the group consisting of norbornene (bicyclo[2.2.1]hept-2-ene), 5-methyl-2-norbornene, ethylnorbornene, propylnorbornene, isopropylnorbornene, butylnorbornene, isobutylnorbornene, pentylnorbornene, hexylnorbornene, heptylnorbornene, octylnorbornene, decylnorbornene, dodecylnorbornene, octadecylnorbornene, p-tolylnorbornene, methylidene norbornene, phenylnorbornene, ethylidenenorbornene, vinylnorbornene, exo-dicyclopentadiene, endo-dicyclopentadiene, tetracyclododecene, methyltetracyclododecene, tetracyclododecadiene, dimethyltetracyclododecene, ethyltetracyclododecene, ethylidenyl tetracyclododecene, phenyltetracyclodecene, symmetrical and unsymmetrical trimers and tetramers of cyclopentadiene, 5,6-dimethylnorbornene, propenylnorbornene, 5,8-methylene-5a,8a-dihydrofluorene, cyclohexenylnorbornene, dimethanohexahydronaphthalene, endo,exo-5,6-dimethoxynorbornene, endo,endo-5,6-dimethoxynorbornene, 2,3-dimethoxynorbornadiene, 5,6-bis(chloromethyl)bicyclo[2.2.1]hept-2-ene, 5-tris(ethoxy)silylnorbornene, 2-dimethylsilylbicyclo[2.2.1]hepta-2,5-diene, 2,3-bistrifluoromethylbicyclo[2.2.1]hepta-2,5-diene, 5-fluoro-5-pentafluoroethyl-6-,6-bis(trifluoromethyl)bicyclo[2.2.1]hept-2-ene, 5,6-difluoro-5-heptatafluoroisopropyl-6-trifluoromethyl)bicyclol[2.2.1]hept-2-ene, 2,3,3,4,4,5,5,6-octafluorotricyclo[5.2.1.O]dec-8-ene, and 5-trifluoromethylbicyclo[2.2.1]hept-2-ene, 5,6-dimethyl-2-norbornene, 5-a-naphthyl-2-norbornene, 5,5-dimethyl-2-norbornene, 1,4,4a,9,9a,10-hexahydro-9,10[1',2']-benzeno-1,4-methanoanthracene. indanylnorbornene (i.e., 1,4,4,9-tetrahydro-1,4-methanofluorene, the reaction product of CPD and indene), 6,7,10,10-tetrahydro-7,10-methanofluoranthene (i.e., the reaction product of CPD with acenaphthalene), 1,4,4,9,9,10-hexahydro-9,10[1',2']-benzeno-1,4-methanoanthracene, endo,endo-5,6-dimethyl-2-norbornene, endo,exo-5,6-dimethyl-2-norbornene, exo,exo-5,6-dimethyl-2-norbornene, 1,4,4,5,6,9,10,13,14,14-decahydro-1,4-methanobenzocyclododecene (i.e., reaction product of CPD and 1,5,9-cyclododecatriene), 2,3,3,4,7,7-hexahydro-4,7-methano-1H-indene (i.e., reaction product of CPD and cyclopentene), 1,4,4,5,6,7,8,8-octahydro-1,4-methanonaphthalene (i.e., reaction product of CPD and cyclohexene), 1,4,4,5,6,7,8,9,10,10-decahydro-1,4-methanobenzocyclooctene, and 1,2,3,3,3,4,7,7,8,8,-decahydro-4,7-methanocyclopent[a]indene.

18. The process of claim 1 wherein the metathesis initiator is any Ru or Os metal carbene metathesis catalyst.

19. The process of claim 18 wherein the metathesis catalyst is tetra-coordinated, penta-coordinated or hexa-coordinated.

20. The process of claim 18 wherein the catalyst possesses a metal center that is in the +2 oxidation state, has an electron count of 16, and is pentacoordinated.

21. The process of claim 20 wherein the catalyst is of the general formula $$X^1_{\prime\prime\prime}\underset{L}{\overset{L^1}{\underset{|}{M}}}\!\!=\!\!C\!\!\underset{R^1}{\overset{R}{\diagdown}} \quad \text{or} \quad X^1_{\prime\prime\prime}\underset{L}{\overset{L^1}{\underset{|}{M}}}\!\!=\!\!C\!\!=\!\!C\!\!\underset{R^1}{\overset{R}{\diagdown}} \quad \text{or}$$

$$X^1_{\prime\prime\prime}\underset{L}{\overset{L^1}{\underset{|}{M}}}\!\!=\!\!C\!\!=\!\!C\!\!\underset{R^1}{\overset{R}{\diagdown}} \quad \text{or} \quad X^1_{\prime\prime\prime}\underset{L}{\overset{L^1}{\underset{|}{M}}}\!\!=\!\!C\!\!=\!\!C\!\!=\!\!C\!\!\underset{R^1}{\overset{R}{\diagdown}}$$

wherein:
M is ruthenium or osmium;
X and $X^1$ are the same or different and are each independently any anionic ligand;
L and $L^1$ are the same or different and are each independently any neutral electron donor ligand;
R and $R^1$ are the same or different and are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl, $C_1$–$C_{20}$ alkylsulfinyl, and silyl, and wherein R and $R^1$ are each independently substituted or unsubstituted.

22. The process of claim 20 wherein the initiator is selected from the group consisting of Ru 575

Ru 595

Ru 716

Ru 731

Ru 751

Ru 779

Ru 799

Ru 801

Ru 815

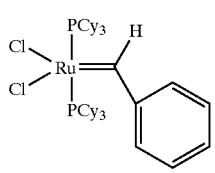
Ru 823

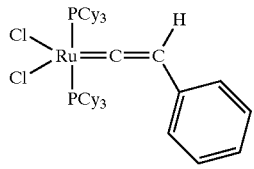
Ru 835

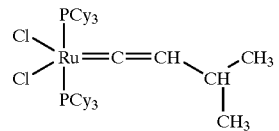
Ru 801(B)

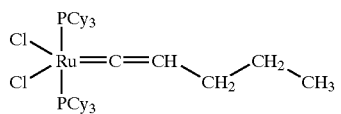
Ru 801(C)

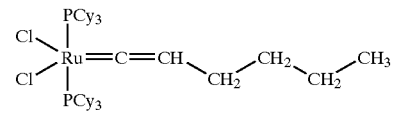
Ru 815(B)

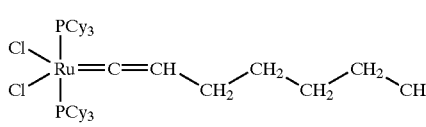
Ru 843 and

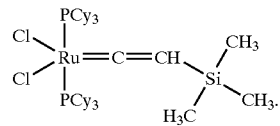
Ru 831

23. The process of claim 1 wherein the reaction occurs in the absence of a solvent.

24. The process of claim 1 wherein the olefin is a polymerizable monomer composition comprising more than one norbornene-type monomers wherein the norbornene-type monomers are the same or different.

25. A process for converting a less active or slower to initiate catalyst system to a higher activity catalyst system, the process comprising contacting a protected N-heterocyclic carbene with a tetra-coordinated metathesis initiator and an olefin in the presence of energy, wherein the protected N-heterocyclic carbene is of the formula NHC—$X^2$—Y, NHC is any N-heterocyclic carbene ligand, and $X^2$—Y is any moiety that is released in the presence of energy.

26. The process of claim 25 wherein the olefin is substituted or unsubstituted norbornene.

27. The process of claim 25 wherein the olefin is substituted or unsubstituted dicyclopentadiene.

28. A process for converting a less active or slower to initiate catalyst system to a higher activity catalyst system, the process comprising contacting a protected N-heterocyclic carbene with a metathesis initiator and an acyclic olefin in the presence of energy, wherein the protected N-heterocyclic carbene is of the formula NHC—$X^2$—Y, NHC is any N-heterocyclic carbene ligand, and $X^2$—Y is any moiety that is released in the presence of energy.

* * * * *